(12) United States Patent
Boehringer et al.

(10) Patent No.: US 7,718,659 B2
(45) Date of Patent: May 18, 2010

(54) HETEROARYLACETAMIDE INHIBITORS OF FACTOR XA

(75) Inventors: Markus Boehringer, Moehlin (CH); Katrin Groebke Zbinden, Basel (CH); Wolfgang Haap, Loerrach (DE); Hans Hilpert, Muenchenstein (CH); Narendra Panday, Basel (CH); Fabienne Ricklin, Hombourg (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 1 day.

(21) Appl. No.: 12/025,124

(22) Filed: Feb. 4, 2008

(65) Prior Publication Data

US 2008/0146550 A1 Jun. 19, 2008

Related U.S. Application Data

(62) Division of application No. 11/301,560, filed on Dec. 13, 2005, now Pat. No. 7,361,672.

(30) Foreign Application Priority Data

Dec. 23, 2004 (EP) ................. 04106943

(51) Int. Cl.
  *A61K 31/381* (2006.01)
  *C07D 417/12* (2006.01)
(52) U.S. Cl. ................. 514/254.02; 544/367

(58) Field of Classification Search ............ 544/359, 544/360
See application file for complete search history.

(56) References Cited

U.S. PATENT DOCUMENTS

2006/0111411 A1  5/2006  Cooper et al.

FOREIGN PATENT DOCUMENTS

| WO | WO 01/12189 | 2/2001 |
|----|-------------|--------|
| WO | WO 01/36386 | 5/2001 |
| WO | WO 02/12196 | 2/2002 |
| WO | WO 2004/031145 | 4/2004 |

OTHER PUBLICATIONS

Cheng et al., Biochem. Pharmacol., 22, pp. 3099-3108 (1973).
Lottenberg et al., Biochem. Biophys. Acta, 742, pp. 539-557 (1983).
Eadie, G.S., J. Biol. Chem., 146, pp. 85-93 (1942).
Database CA Registry (online), Jun. 12, 2001, XP002385272.

*Primary Examiner*—Rebecca L Anderson
*Assistant Examiner*—Shawquia Young
(74) *Attorney, Agent, or Firm*—George W. Johnston; Dennis P. Tramaloni; Brian C. Remy

(57) ABSTRACT

The invention is concerned with novel heteroarylacetamides of formula (I)

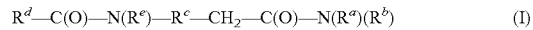

$$R^d\text{—}C(O)\text{—}N(R^c)\text{—}R^e\text{—}CH_2\text{—}C(O)\text{—}N(R^a)(R^b) \qquad (I)$$

wherein $R^a$ to $R^e$ are as defined in the description and in the claims, as well as physiologically acceptable salts thereof. These compounds inhibit the coagulation factor Xa and can be used as medicaments.

20 Claims, No Drawings

HETEROARYLACETAMIDE INHIBITORS OF FACTOR XA

PRIORITY TO RELATED APPLICATIONS

This application is a division of U.S. application Ser. No. 11/301,560, filed Dec. 13, 2005, which claims the benefit of European Application No. 04106943.6, filed Dec. 23, 2004. The entire contents of the above-identified applications are hereby incorporated by reference.

SUMMARY OF THE INVENTION

The invention is concerned with novel heteroarylacetamides of formula (I),

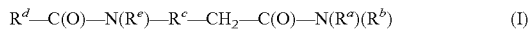

$$R^d-C(O)-N(R^e)-R^c-CH_2-C(O)-N(R^a)(R^b) \quad (I)$$

wherein $R^a$ is hydrogen or $C_{1-6}$ alkyl;

$R^b$ is $R^{b1}$-$R^{b2}$, wherein $R^{b1}$ is aryl or heteroaryl, said aryl and heteroaryl being optionally substituted by one or more substituents independently selected from the group consisting of $C_{1-6}$ alkyl and halogen, and $R^{b2}$ is aryl, heteroaryl or heterocyclyl, said aryl, heteroaryl and heterocyclyl being optionally substituted by one or more substituents independently selected from the group consisting of $C_{1-6}$ alkyl, $C_{2-6}$ alkenyl, $C_{2-6}$ alkynyl, $C_{1-6}$ alkoxy, halogen, cyano, nitro, amino, mono- or di-$C_{1-6}$ alkyl substituted amino, hydroxy, hydroxy $C_{1-6}$ alkyl, aminocarbonyl, mono- or di-$C_{1-6}$ alkyl substituted aminocarbonyl, halo $C_{1-6}$ alkyl, $C_{1-6}$ alkylsulfonyl, $C_{1-6}$ alkylsulfinyl, $C_{1-6}$ alkylthio, amino $C_{1-6}$ alkyl, mono- or di-$C_{1-6}$ alkyl substituted amino $C_{1-6}$ alkyl, aminosulfonyl and mono- or di-$C_{1-6}$ alkyl substituted amino sulfonyl, wherein one or two carbon atoms of said aryl, heteroaryl and heterocyclyl can optionally be replaced with a carbonyl group;

or $R^a$ and $R^b$, together with the nitrogen atom to which they are attached, form heterocyclyl-A-$R^{b3}$, wherein said heterocyclyl can optionally be substituted by halogen or $C_{1-6}$ alkyl, and A is a bond, —O— or $C_{1-6}$ alkylene wherein one —CH$_2$— can optionally be replaced with a carbonyl group, and/or another —CH$_2$— can optionally be replaced with —NR$^f$—, and $R^{b3}$ is amino optionally mono- or di-substituted by a substituent independently selected from the group consisting of $C_{1-6}$ alkyl, $C_{2-6}$ alkenyl and $C_{2-6}$ alkynyl, or $R^{b3}$ is aryl, heteroaryl, $C_{3-7}$ cycloalkyl or heterocyclyl, said aryl, heteroaryl, $C_{3-7}$ cycloalkyl and heterocyclyl being optionally substituted by one or more substituents independently selected from the group consisting of $C_{1-6}$ alkyl, $C_{2-6}$ alkenyl, $C_{2-6}$ alkynyl, $C_{1-6}$ alkoxy, halogen, cyano, nitro, amino, mono- or di-$C_{1-6}$ alkyl substituted amino, hydroxy, hydroxy $C_{1-6}$ alkyl, aminocarbonyl, mono- or di-$C_{1-6}$ alkyl substituted aminocarbonyl, halo $C_{1-6}$ alkyl, $C_{1-6}$ alkylsulfonyl, $C_{1-6}$ alkylsulfinyl, $C_{1-6}$ alkylthio, amino $C_{1-6}$ alkyl, mono- or di-$C_{1-6}$ alkyl substituted amino $C_{1-6}$ alkyl, aminosulfonyl and mono- or di-$C_{1-6}$ alkyl substituted amino sulfonyl, wherein one or two carbon atoms of said aryl, heteroaryl, $C_{3-7}$ cycloalkyl and heterocyclyl can optionally be replaced with a carbonyl group;

$R^c$ is heteroaryl optionally substituted by one or more substituents independently selected from the group consisting of halogen and $C_{1-6}$ alkyl, wherein one or two carbon atoms of said heteroaryl can optionally be replaced with a carbonyl group;

$R^d$ is aryl, heteroaryl or heterocyclyl, said aryl, heteroaryl and heterocyclyl optionally being substituted by one or more substituents independently selected from the group consisting of halogen, $C_{1-6}$ alkyl and $C_{1-6}$ alkoxy, and the aryl may be fused to a heterocyclyl ring;

$R^e$ is hydrogen or $C_{1-6}$ alkyl;

$R^f$ is hydrogen or $C_{1-6}$ alkyl;

and prodrugs and pharmaceutically acceptable salts thereof.

Further, the invention is concerned with a process for the manufacture of the above compounds, pharmaceutical preparations which contain such compounds as well as the use of these compounds for the production of pharmaceutical preparations.

The compounds of formula (I) are active compounds that inhibit the activity of coagulation factor Xa. These compounds consequently influence blood coagulation. They therefore inhibit the formation of thrombi and can be used for the treatment and/or prevention of thrombotic disorders, such as amongst others, arterial and venous thrombosis, deep vein thrombosis, peripheral arterial occlusive disease (PAOD), unstable angina pectoris, myocardial infarction, coronary artery disease, pulmonary embolism, stroke (cerebral thrombosis) due to atrial fibrillation, inflammation and arteriosclerosis. They have potentially benefit in the treatment of acute vessel closure associated with thrombolytic therapy and restenosis, e.g. after transluminal coronary angioplasty (PTCA) or bypass grafting of the coronary or peripheral arteries and in the maintenance of vascular access patency in long term hemodialysis patients. Factor Xa inhibitors of this invention may form part of a combination therapy with an anticoagulant with a different mode of action or with a platelet aggregation inhibitor or with a thrombolytic agent. Furthermore, these compounds have an effect on tumor cells and prevent metastases. They can therefore also be used as antitumor agents.

Other inhibitors of factor Xa had previously been suggested for the inhibition of the formation of thrombi and for the treatment of related diseases. However, there is still a need for novel factor Xa inhibitors which exhibit improved pharmacological properties, e.g. an improved selectivity towards thrombin.

The present invention provides novel compounds of formula (I) which are factor Xa inhibitors. The compounds of the present invention unexpectedly inhibit coagulation factor Xa and also exhibit improved pharmacological properties compared to other compounds already known in the art.

DETAILED DESCRIPTION OF THE INVENTION

All patents, patent applications, and publications cited herein are incorporated by reference in their entirety. In the event of a conflict in teaching, the present disclosure is controlling.

Unless otherwise indicated, the following definitions are set forth to illustrate and define the meaning and scope of the various terms used to describe the invention herein.

DEFINITIONS

The term "halogen" or "halo" means fluorine, chlorine, bromine and iodine, with fluorine, chlorine and bromine being preferred, and fluorine and chlorine being more preferred.

The term "$C_{1-6}$ alkyl", alone or in combination with other groups, means a branched or straight-chain monovalent alkyl radical, having one to six carbon atoms. This term is further exemplified by such radicals as methyl, ethyl, n-propyl, isopropyl, n-butyl, s-butyl, t-butyl. $C_{1-4}$ alkyl is more preferred.

The term "$C_{1-6}$ alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene.

The term "halo $C_{1-6}$ alkyl" means $C_{1-6}$ alkyl substituted by one or more same or different halogen atoms independently selected from the group consisting of chlorine, fluorine and bromine. $CF_3$ is preferred.

The term "$C_{3-7}$ cycloalkyl", alone or in combination with other groups, means a saturated monovalent cyclic hydrocarbon radical of three to seven ring carbons, e.g., cyclopropyl, cyclobutyl, cyclohexyl.

The term "$C_{1-6}$ alkoxy", alone or in combination with other groups, means the group R'—O—, wherein R' is a $C_{1-6}$ alkyl.

The term "$C_{2-6}$ alkenyl", alone or in combination with other groups, means a straight-chain or branched hydrocarbon residue comprising an olefinic bond, having two to six carbon atoms, such as e.g. ethenyl, 2-propenyl.

The term "$C_{2-6}$ alkynyl", alone or in combination with other groups, means a straight-chain or branched hydrocarbon residue comprising a triple bond, having two to six carbon atoms, such as e.g. ethynyl, propynyl.

The term "aryl", alone or in combination with other groups, means a phenyl or a naphthyl group, preferably a phenyl group.

The term "heterocyclyl", alone or combination with other groups, means non-aromatic mono- or bi-cyclic radicals of three to eight ring atoms in which one or two ring atoms are heteroatoms selected from N, O, or $S(O)_n$ (where n is an integer from 0 to 2), the remaining ring atoms being C.

The term "heteroaryl", alone or combination with other groups, means a monocyclic or bicyclic radical of 5 to 12 ring atoms having at least one aromatic ring containing one, two, or three ring heteroatoms selected from N, O, and S, the remaining ring atoms being C, with the understanding that the attachment point of the heteroaryl radical will be on an aromatic ring.

The term "mono-$C_{1-6}$ alkyl substituted amino" and "di-$C_{1-6}$ alkyl substituted amino", alone or combination with other groups, mean —NHR and —NRR' respectively, in which R and R' are the same or different $C_{1-6}$ alkyl.

Preferred radicals for the chemical groups whose definitions are given above are those specifically exemplified in Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) in which a COOH group is present can further form salts with bases. Examples of such salts are alkaline, earth-alkaline and ammonium salts such as e.g. Na—, K—, Ca— and Trimethylammonium salts. The term "pharmaceutically acceptable salts" also refers to such salts. Acid addition salts as described above are preferred.

"Optional" or "optionally" means that the subsequently described event or circumstance may but need not occur, and that the description includes instances where the event or circumstance occurs and instances in which it does not. For example, "aryl group that can optionally be substituted with an alkyl group" means that the alkyl may but need not be present, and the description includes situations where the aryl group is substituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Compounds that have the same molecular formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula (I) can possess one or more asymmetric centers. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

While the broadest definition of this invention is described before, certain compounds of Formula (I) are preferred.

i) A preferred compound of the invention is a compound of Formula (I) wherein $R^a$ and $R^b$, together with the nitrogen atom to which they are attached, form heterocyclyl-A-$R^{b3}$, wherein said heterocyclyl can optionally be substituted by halogen or $C_{1-6}$ alkyl, and A and $R^{b3}$ are as defined before.

The heterocyclyl of heterocyclyl-A-$R^{b3}$ is preferably piperazinyl or piperidinyl, said piperazinyl and piperidinyl being optionally substituted by one or more substituents independently selected from the group consisting of halogen and $C_{1-6}$ alkyl, especially non substituted piperazinyl or non substituted piperidinyl. Piperazin-1-yl or piperidin-1-yl, said piperazin-1-yl and piperidin-1-yl being bonded to -A-$R^{b3}$ at 4-position is especially preferred.

A is preferably a bond or $C_{1-6}$ alkylene wherein one —$CH_2$— can optionally be replaced with a carbonyl group, and/or another —$CH_2$— can optionally be replaced with —$NR^f$—, in which $R^f$ is hydrogen or $C_{1-6}$ alkyl. A is more preferably a bond, methylene, ethylene, —$CH_2$—C(O)—, —C(O)—$CH_2$— or —C(O)—, especially a bond or —$CH_2$—C(O)—.

$R^{b3}$ is preferably heterocyclyl optionally substituted by one or more substituents independently selected from the group consisting of $C_{1-6}$ alkyl, $C_{1-6}$ alkoxy, amino, mono- or di-$C_{1-6}$ alkyl substituted amino, hydroxy, hydroxy $C_{1-6}$ alkyl, aminocarbonyl, mono- or di-$C_{1-6}$ alkyl substituted aminocarbonyl, halo $C_{1-6}$ alkyl, $C_{1-6}$ alkylsulfonyl, $C_{1-6}$ alkylsulfinyl, $C_{1-6}$ alkylthio, and one or two carbon atoms of said heterocyclyl being optionally replaced with a carbonyl group. Heterocyclyl for $R^{b3}$ is preferably one having a nitrogen as a ring member atom, such as piperidinyl, pyrrolidinyl, morpholinyl, piperazinyl or thiazolidinyl, said heterocyclyl group being optionally substituted by one or more substituents, preferably one substituent independently selected from the group consisting of $C_{1-6}$ alkyl, $C_{1-6}$ alkoxy, amino, mono- or di-$C_{1-6}$ alkyl substituted amino, hydroxy, hydroxy $C_{1-6}$ alkyl, aminocarbonyl, mono- or di-$C_{1-6}$ alkyl substituted aminocarbonyl, halo $C_{1-6}$ alkyl, $C_{1-6}$ alkylsulfonyl, $C_{1-6}$ alkylsulfinyl, $C_{1-6}$ alkylthio, and one or two carbon atoms of said heterocyclyl group being optionally replaced with a carbonyl group.

Heterocyclyl for $R^{b3}$ is more preferably pyrrolidinyl, piperidinyl or piperazinyl, said heterocyclyl groups being unsubstituted or substituted by one $C_{1-6}$ alkyl. Especially preferred are non substituted pyrrolidin-1-yl and 1-methyl-piperidin-4-yl.

ii) Another preferred compound of the invention is a compound of Formula (I) wherein $R^a$ is hydrogen or $C_{1-6}$ alkyl, and $R^b$ is $R^{b1}$-$R^{b2}$, wherein $R^{b1}$ and $R^{b2}$ are as defined before. $R^a$ is preferably hydrogen.

$R^{b1}$ is preferably phenyl or pyridyl, said phenyl and pyridyl being optionally substituted by one or more substituents independently selected from the group consisting of $C_{1-6}$ alkyl and halogen, preferably optionally substituted by one halogen atom. $R^{b1}$ is more preferably phenyl optionally substituted by one or more halogen atoms, preferably one halogen atom, especially fluorine.

$R^{b2}$ is preferably aryl, heteroaryl or heterocyclyl, more preferably heteroaryl or heterocyclyl, said aryl, heteroaryl and heterocyclyl being optionally substituted by one or more substituents, preferably one substituent independently selected from the group consisting of $C_{1-6}$ alkylsulfonyl, $C_{1-6}$ alkylsulfinyl, $C_{1-6}$ alkylthio, amino $C_{1-6}$ alkyl, mono- or di-$C_{1-6}$ alkyl substituted amino $C_{1-6}$ alkyl, aminosulfonyl, mono- or di-$C_{1-6}$ alkyl substituted amino sulfonyl, and one or two carbon atoms of said aryl, heteroaryl and heterocyclyl being optionally replaced with a carbonyl group. A preferred aryl for $R^{b2}$ is phenyl optionally substituted by one substituent selected from the group consisting of $C_{1-6}$ alkylsulfonyl, aminosulfonyl and mono- or di-$C_{1-6}$ alkyl substituted amino sulfonyl.

$R^{b2}$ is more preferably heteroaryl or heterocyclyl having a ring member nitrogen atom bonded to $R^{b1}$, said heteroaryl and heterocyclyl being optionally substituted by one or more substituents independently selected from the group consisting of $C_{1-6}$ alkylsulfonyl, $C_{1-6}$ alkylsulfinyl, $C_{1-6}$ alkylthio, amino $C_{1-6}$ alkyl, mono- or di-$C_{1-6}$ alkyl substituted amino $C_{1-6}$ alkyl, aminosulfonyl and mono- or di-$C_{1-6}$ alkyl substituted amino sulfonyl, and one or two carbon atoms of said heteroaryl and heterocyclyl being optionally replaced with a carbonyl group.

A preferred heteroaryl for $R^{b2}$ is a mono cyclic heteroaryl having one or two nitrogen atoms as a ring member such as pyridyl, imidazolyl, pyrrolyl, pyrazolyl, pyrazinyl, pyrimidinyl, pyridazinyl, preferably pyridyl or imidazolyl, especially pyridyl. Preferably said heteroaryl is attached to $R^{b1}$ via the nitrogen atom, and unsubstituted or substituted by amino $C_{1-6}$ alkyl or mono- or di-$C_{1-6}$ alkyl substituted amino $C_{1-6}$ alkyl. Moreover, preferably one carbon atom of said heteroaryl is replaced with a carbonyl group. 2-oxo-2H-pyridin-1-yl is especially preferred.

A preferred heterocyclyl for $R^{b2}$ is a mono cyclic heterocyclyl having one nitrogen atom and, in addition to it, oxygen and/or sulphur atom as a ring member such as morpholinyl, 1,1-dioxo-thiazianyl, 1,1-dioxo-isothiazolidinyl, 3-oxomorpholinyl. Preferably said heterocyclyl is attached to $R^{b1}$ via the nitrogen atom, and unsubstituted. In addition, preferably one carbon atom of the heterocyclyl for $R^{b2}$ is replaced with a carbonyl group at the position adjacent to the ring member atom attached to $R^{b1}$, or the heterocyclyl for $R^{b2}$ has —$SO_2$— as a ring member at the position adjacent to the ring member atom attached to $R^{b1}$.

iii) Another preferred compound of the invention is a compound of Formula (I) wherein $R^e$ is hydrogen.

iv) Another preferred compound of the invention is a compound of Formula (I) wherein $R^c$ is mono cyclic heteroaryl having a nitrogen atom and/or a sulphur atom as a ring member atom such as thiazolyl, pyrazolyl, triazolyl, tetrazolyl, pyridonyl. Triazolyl is especially preferred.

v) Another preferred compound of the invention is a compound of Formula (I) wherein $R^d$ is aryl, preferably phenyl, or heteroaryl, preferably thienyl, pyridyl or indolyl, especially thienyl, said aryl and heteroaryl being optionally substituted by one or more substituents, preferably one substituent, independently selected from the group consisting of halogen, $C_{1-6}$ alkyl and $C_{1-6}$ alkoxy.

A preferred aryl for $R^d$ is phenyl substituted by one halogen atom such as fluorine, bromine, chlorine, preferably chlorine. 4-chlorophenyl is especially preferred.

A preferred heteroaryl for $R^d$ is thienyl, pyridyl or indolyl, said heteroaryls being optionally substituted by one halogen atom such as fluorine, bromine, chlorine, preferably chlorine. 5-chloro-thiophen-2-yl is especially preferred.

Particularly preferred compounds of the present invention are:

[4-(2-[1,4']-Bipiperidinyl-1'-yl-2-oxo-ethyl)-thiazol-2-yl]-4-chloro-benzamide,

N-{4-[2-(4-Benzyl-piperazin-1-yl)-2-oxo-ethyl]-thiazol-2-yl}-4-chloro-benzamide, 4-Chloro-N-{4-[2-(4-cyclohexylmethyl-piperazin-1-yl)-2-oxo-ethyl]-thiazol-2-yl}-benzamide, 4-Chloro-N-(4-{2-[4-(2-morpholin-4-yl-ethyl)-piperazin-1-yl]-2-oxo-ethyl}-thiazol-2-yl)-benzamide, 4-Chloro-N-(4-{2-oxo-2-[4-(2-oxo-2-pyrrolidin-1-yl-ethyl)-piperazin-1-yl]-ethyl}-thiazol-2-yl)-benzamide, 4-Chloro-N-(4-{2-oxo-2-[4-(2-oxo-2-pyrrolidin-1-yl-ethyl)-piperazin-1-yl]-ethyl}-thiazol-2-yl)-benzamide, 4-Chloro-N-(4-{2-oxo-2-[4-(2-oxo-2-pyrrolidin-1-yl-ethyl)-piperazin-1-yl]-ethyl}-thiazol-2-yl)-benzamide, 4-Chloro-{4-[2-(4-cyclopentyl-piperazin-1-yl)-2-oxo-ethyl]-thiazol-2-yl}-benzamide, 4-Chloro-N-(4-{2-[4-(2-morpholin-4-yl-2-oxo-ethyl)-piperazin-1-yl]-2-oxo-ethyl}-thiazol-2-yl)-benzamide, 4-Chloro-N-{4-[2-(4-dimethylcarbamoylmethyl-piperazin-1-yl)-2-oxo-ethyl]-thiazol-2-yl}-benzamide, 4-Chloro-N-[4-(2-{4-[2-(4-methyl-piperazin-1-yl)-2-oxo-ethyl]-piperazin-1-yl}-2-oxo-ethyl)-thiazol-2-yl]-benzamide, 4-Chloro-N-[4-(2-{4-[(1-methyl-piperidin-4-ylcarbamoyl)-methyl]-piperazin-1-yl}-2-oxo-ethyl)-thiazol-2-yl]-benzamide, 4-Chloro-N-[4-(2-{4-[(1-methyl-piperidin-4-ylcarbamoyl)-methyl]-piperazin-1-yl}-2-oxo-ethyl)-thiazol-2-yl]-benzamide, 4-Chloro-N-[4-(2-oxo-2-{4-[2-(2-oxo-pyrrolidin-1-yl)-acetyl]-piperazin-1-yl}-ethyl)-thiazol-2-yl]-benzamide, 3-Fluoro-4-methoxy-(4-{2-oxo-2-[4-(2-oxo-2-pyrrolidin-1-yl-ethyl)-piperazin-1-yl]-ethyl}-thiazol-2-yl)-benzamide, 4-Chloro-N-[4-(2-{4-[2-(cyclohexylmethyl-amino)-acetyl]-piperazin-1-yl}-2-oxo-ethyl)-thiazol-2-yl]-benzamide, 4-Methoxy-(4-{2-oxo-2-[4-(2-oxo-2-pyrrolidin-1-yl-ethyl)-piperazin-1-yl]-ethyl}-thiazol-2-yl)-benzamide, 5-Chloro-thiophene-2-carboxylic acid (4-{2-oxo-2-[4-(2-oxo-2-pyrrolidin-1-yl-ethyl)-piperazin-1-yl]-ethyl}-thiazol-2-yl)-amide, 5-Chloro-thiophene-2-carboxylic acid (4-{2-oxo-2-[4-(2-oxo-2-pyrrolidin-1-yl-ethyl)-piperazin-1-yl]-ethyl}-thiazol-2-yl)-amide, 2,3-Dihydro-benzofuran-5-carboxylic acid (4-{2-oxo-2-[4-(2-oxo-2-pyrrolidin-1-yl-ethyl)-piperazin-1-yl]-ethyl}-thiazol-2-yl)-amide, 4-Chloro-N-(4-{2-oxo-2-[4-(2-pyrrolidin-1-yl-acetyl)-piperazin-1-yl]-ethyl}-thiazol-2-yl)-benzamide, 5-Chloro-pyridine-2-carboxylic acid (4-{2-oxo-2-[4-(2-oxo-2-pyrrolidin-1-yl-ethyl)-piperazin-1-yl]-ethyl}-thiazol-2-yl)-amide, 4-Chloro-(RS)-[4-(2-{4-[2-(3-dimethylamino-pyrrolidin-1-yl)-2-oxo-ethyl]-piperazin-1-yl}-2-oxo-ethyl)-thiazol-2-yl]-benzamide, 4-Chloro-(RS)-[4-(2-{4-[2-(3-hydroxy-pyrrolidin-1-yl)-2-oxo-ethyl]-piperazin-1-yl}-2-oxo-ethyl)-thiazol-2-yl]-benzamide, 4-Chloro-[4-(2-{4-[2-((R)-2-hydroxymethyl-pyrrolidin-1-yl)-2-oxo-ethyl]-piperazin-1-yl}-2-oxo-ethyl)-thiazol-2-yl]-benzamide, 4-Chloro-[4-(2-{4-[2-((S)-2-hydroxymethyl-pyrrolidin-1-yl)-2-oxo-ethyl]-piperazin-1-yl}-2-oxo-ethyl)-thiazol-2-yl]-benzamide, 4-Chloro-[4-(2-{4-[2-(2,2-dimethyl-thiazolidin-3-yl)-2-oxo-ethyl]-piperazin-1-yl}-2-oxo-ethyl)-thiazol-2-yl]-benzamide, 4-Chloro-N-(4-{[2-fluoro-4-(2-oxo-2H-pyridin-1-yl)-phenylcarbamoyl]-methyl}-thiazol-2-yl)-benzamide, 4-Chloro-N-(4-{[2-fluoro-4-(2-oxo-2H-pyridin-1-yl)-phenylcarbamoyl]-methyl}-thiazol-2-yl)-benzamide, N-{4-[(2'-tert-Butylsulfamoyl-3-fluoro-biphenyl-4-ylcarbamoyl)-methyl]-thiazol-2-yl}-4-chloro-benzamide, (S)-1-[2-(4-{2-[2-(4-Chloro-benzoylamino)-thiazol-4-yl]-acetyl}-piperazin-1-yl)-acetyl]-pyrrolidine-2-carboxylic acid dimethylamide, 4-Chloro-N-{4-[(3-fluoro-2'-sulfamoyl-biphenyl-4-ylcarbamoyl)-methyl]-thiazol-2-yl}-benzamide, 4-Chloro-N-(4-{2-[4-(1-methyl-piperidin-4-yl)-piperazin-1-yl]-2-oxo-ethyl}-thiazol-2-yl)-benzamide, Benzo[1,3]dioxole-5-carboxylic acid (4-{2-oxo-2-[4-(2-oxo-2-pyrrolidin-1-yl-ethyl)-piperazin-1-yl]-ethyl}-thiazol-2-yl)-amide, 5-Methyl-thiophene-2-carboxylic acid (4-{2-oxo-2-[4-(2-oxo-2-pyrrolidin-1-yl-ethyl)-piperazin-1-yl]-ethyl}-thiazol-2-yl)-amide, 5-Bromo-thiophene-2-carboxylic acid (4-{2-oxo-2-[4-(2-oxo-2-pyrrolidin-1-yl-ethyl)-piperazin-1-yl]-ethyl}-thiazol-2-yl)-amide, 4-Chloro-N-[4-(2-oxo-2-{4-[2-(2-oxo-oxazolidin-3-yl)-ethyl]-piperazin-1-yl}-ethyl)-thiazol-2-yl]-benzamide, 4-Chloro-N-(4-{[5-(2-methanesulfonyl-phenyl)-pyridin-2-ylcarbamoyl]-methyl}-thiazol-2-yl)-benzamide, (S)-1-[2-(4-{2-[2-(4-Chloro-benzoylamino)-thiazol-4-yl]-acetyl}-piperazin-1-yl)-acetyl]-pyrrolidine-2-carboxylic acid methylamide, 4-Chloro-[4-(2-{4-[2-(3-methanesulfonyl-pyrrolidin-1-yl)-2-oxo-ethyl]-piperazin-1-yl}-2-oxo-ethyl)-thiazol-2-yl]-benzamide, N-{4-[2-(4-Benzoyl-piperazin-1-yl)-2-oxo-ethyl]-thiazol-2-yl}-4-chloro-benzamide, 4-Chloro-[4-(2-{4-[2-((1S,3R,5R)-3-hydroxy-8-aza-bicyclo[3.2.1]oct-8-yl)-2-oxo-ethyl]-piperazin-1-yl}-2-oxo-ethyl)-thiazol-2-yl]-benzamide, 4-Chloro-[4-(2-{4-[2-((R)-3-ethoxy-pyrrolidin-1-yl)-2-oxo-ethyl]-piperazin-1-yl}-2-oxo-ethyl)-thiazol-2-yl]-benzamide, 1H-Indole-6-carboxylic acid (4-{2-oxo-2-[4-(2-oxo-2-pyrrolidin-1-yl-ethyl)-piperazin-1-yl]-ethyl}-thiazol-2-yl)-amide, 4-Chloro-3-fluoro-N-(4-{2-oxo-2-[4-(2-oxo-2-pyrrolidin-1-yl-ethyl)-piperazin-1-yl]-ethyl}-thiazol-2-yl)-benzamide, 4-Chloro-(4-{2-oxo-2-[4-(2-oxo-2-thiazolidin-3-yl-ethyl)-piperazin-1-yl]-ethyl}-thiazol-2-yl)-benzamide,

[4-(2-{4-[2-(3-Amino-pyrrolidin-1-yl)-2-oxo-ethyl]-piperazin-1-yl}-2-oxo-ethyl)-thiazol-2-yl]-4-chloro-benzamide, 4-Chloro-[4-(2-oxo-2-{4-[2-oxo-2-((R)-2-trifluoromethyl-pyrrolidin-1-yl)-ethyl]-piperazin-1-yl}-ethyl)-thiazol-2-yl]-benzamide, 4-Chloro-N-(4-{2-[4-(4,5-dihydro-thiazol-2-yl)-piperazin-1-yl]-2-oxo-ethyl}-thiazol-2-yl)-benzamide, 5-Bromo-thiophene-2-carboxylic acid (4-{2-[4-(1-methyl-piperidin-4-yl)-piperazin-1-yl]-2-oxo-ethyl}-thiazol-2-yl)-amide, 5-Chloro-thiophene-2-carboxylic acid (4-{2-[4-(1-methyl-piperidin-4-yl)-piperazin-1-yl]-2-oxo-ethyl}-thiazol-2-yl)-amide, 5-Chloro-thiophene-2-carboxylic acid (4-{2-[4-(1-methyl-piperidin-4-yl)-piperazin-1-yl]-2-oxo-ethyl}-thiazol-2-yl)-amide, 3-Fluoro-4-methoxy-N!-(4-{2-[4-(1-methyl-piperidin-4-yl)-piperazin-1-yl]-2-oxo-ethyl}-thiazol-2-yl)-benzamide, 4-Chloro-(4-{[4-(2-dimethylaminomethyl-imidazol-1-yl)-2-fluoro-phenylcarbamoyl]-methyl}-thiazol-2-yl)-benzamide, 4-Chloro-(4-{[2-fluoro-4-(3-oxo-morpholin-4-yl)-phenylcarbamoyl]-methyl}-thiazol-2-yl)-benzamide, 4-Chloro-(4-{[4-(1,1-dioxo-[1,2]thiazinan-2-yl)-phenylcarbamoyl]-methyl}-thiazol-2-yl)-benzamide, 4-Chloro-(4-{[4-(1,1-dioxo-isothiazolidin-2-yl)-phenylcarbamoyl]-methyl}-thiazol-2-yl)-benzamide, 5-Methyl-thiophene-2-carboxylic acid (4-{2-[4-(1-methyl-piperidin-4-yl)-piperazin-1-yl]-2-oxo-ethyl}-thiazol-2-yl)-amide, 4-Chloro-(4-{2-[4-(4-methyl-piperazin-1-yl)-piperidin-1-yl]-2-oxo-ethyl}-thiazol-2-yl)-benzamide, 5-Chloro-thiophene-2-carboxylic acid (4-{[2-fluoro-4-(2-oxo-2H-pyridin-1-yl)-phenylcarbamoyl]-methyl}-thiazol-2-yl)-amide, 4-Chloro-N-(4-{2-oxo-2-[4-(pyridin-2-yloxy)-piperidin-1-yl]-ethyl}-thiazol-2-yl)-benzamide, 5-Chloro-thiophene-2-carboxylic acid (4-{2-[4-(4-methyl-piperazin-1-yl)-piperidin-1-yl]-2-oxo-ethyl}-thiazol-2-yl)-amide, 5-Chloro-thiophene-2-carboxylic acid (4-{[2-fluoro-4-(3-oxo-morpholin-4-yl)-phenylcarbamoyl]-methyl}-thiazol-2-yl)-amide, 4-Chloro-N-(1-{2-[4-(1-methyl-piperidin-4-yl)-piperazin-1-yl]-2-oxo-ethyl}-1H-pyrazol-3-yl)-benzamide, 5-Chloro-thiophene-2-carboxylic acid (1-{2-[4-(1-methyl-piperidin-4-yl)-piperazin-1-yl]-2-oxo-ethyl}-1H-pyrazol-3-yl)-amide, 5-Chloro-thiophene-2-carboxylic acid (1-{[2-fluoro-4-(2-oxo-2H-pyridin-1-yl)-phenylcarbamoyl]-methyl}-1H-pyrazol-3-yl)-amide, 4-Chloro-N-(1-{[2-fluoro-4-(2-oxo-2H-pyridin-1-yl)-phenylcarbamoyl]-methyl}-1H-pyrazol-3-yl)-benzamide, 5-Chloro-thiophene-2-carboxylic acid (1-{2-[4-(1-methyl-piperidin-4-yl)-piperazin-1-yl]-2-oxo-ethyl}-1H-[1,2,4]triazol-3-yl)-amide, 5-Chloro-thiophene-2-carboxylic acid (1-{[2-fluoro-4-(2-oxo-2H-pyridin-1-yl)-phenylcarbamoyl]-methyl}-1H-[1,2,4]triazol-3-yl)-amide, 5-Chloro-thiophene-2-carboxylic acid (2-{[2-fluoro-4-(2-oxo-2H-pyridin-1-yl)-phenylcarbamoyl]-methyl}-2H-tetrazol-5-yl)-amide.

The compounds of the present invention can be prepared, for example, by the general synthetic procedures described below.

General Synthetic Procedures

Abbreviations

BOP: Benzotriazolyl-N-oxy-tris(dimethylamino)-phosphonium hexafluorophosphate

BOP-Cl: Bis-(2-oxo-3-oxazolidinyl)-phosphinic acid chloride

DIPEA: Diisopropyl ethyl amine

DMF: N,N-Dimethylformamide

EDCI: N-(3-Dimethylaminopropyl)-N'-ethyl-carbodiimide hydrochloride

PyBOP: Benzotriazol-1-yl-oxytripyrrolidinephosphonium hexafluorophosphate

TEA: Triethylamine

TBTU: O-(Benzotriazol-1-yl)-N,N,N',N'-tetramethyluronium terafluoroborate

THF: Tetrahydrofurane

1. Synthesis of Thiazole Derivatives: Route A

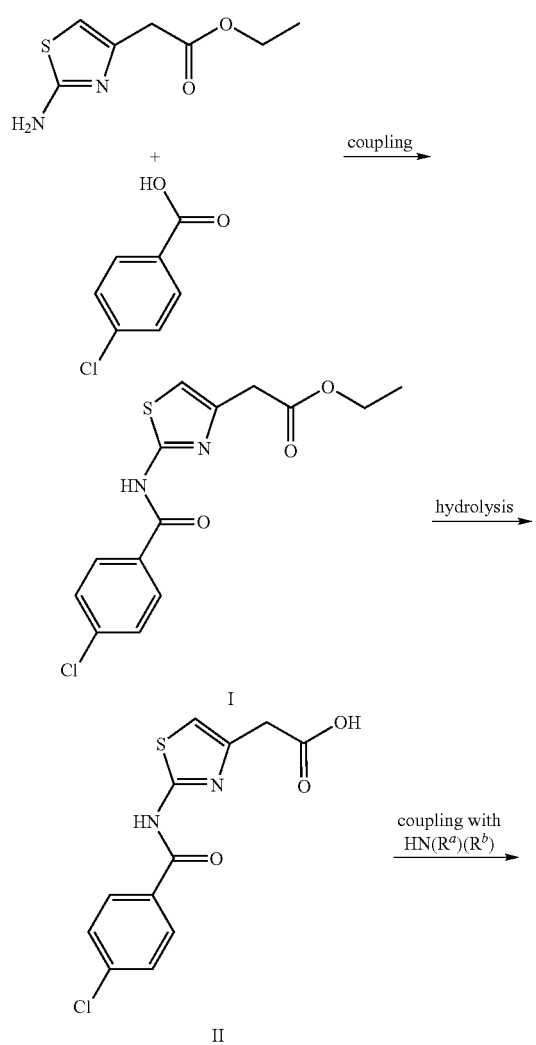

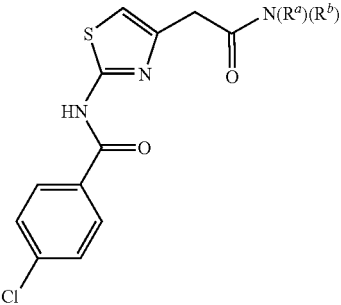

III $R^a$ and $R^b$ in the scheme are as defined before.

The starting acid is dissolved in a suitable solvent such as $CH_2Cl_2$, DMF, acetonitrile, THF and activated with an amide coupling reagent such as BOP, BOP-Cl, TBTU, EDCI/DMAP in the presence of a base like TEA, DIPEA, N-methylmorpholine etc. at 0° C. to 50° C. After adding one to two equivalents 2-(2-aminothiazol-4-yl)-ethyl acetate the corresponding amide is obtained after reaction for 0.5-120 h at 0° C. to 50° C. Preferred conditions are DMF, BOP and DIPEA.

Alkaline hydrolysis of intermediate I is effected by dissolving it in a suitable solvent like MeOH, EtOH, THF, 1,4-dioxane, water or mixtures thereof and a base like LiOH, NaOH, KOH, $Na_2CO_3$, $K_2CO_3$ or $Cs_2CO_3$. Preferred conditions are NaOH in EtOH/$H_2O$.

Intermediate II is then coupled with a primary or secondary amine or aniline HN($R^a$)($R^b$) as described for the preparation of intermediate I. Preferred conditions are DMF, BOP and DIPEA or $CH_2Cl_2$, TBTU and TEA.

2. Synthesis of Thiazole Derivatives: Route B

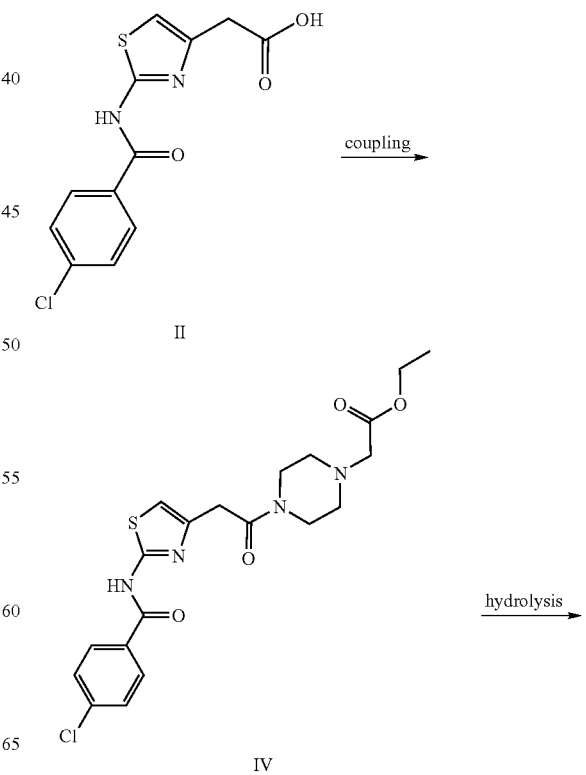

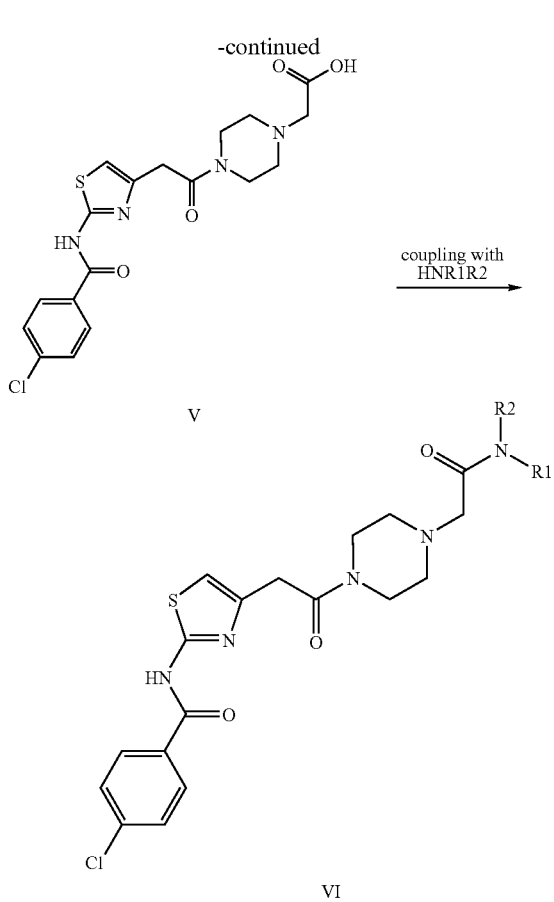

In the scheme shown above, $R^1$ is hydrogen, $C_{1-6}$ alkyl, $C_{2-6}$ alkenyl or $C_{2-6}$ alkynyl and $R^2$ is hydrogen, $C_{1-6}$ alkyl, $C_{2-6}$ alkenyl, $C_{2-6}$ alkynyl, $C_{3-7}$ cycloalkyl $C_{1-6}$ alkyl or heterocyclyl, provided that $R^2$ can be $C_{3-7}$ cycloalkyl $C_{1-6}$ alkyl or heterocyclyl, only when $R^1$ is hydrogen or $C_{1-6}$ alkyl. $R^1$ and $R^2$, together with the nitrogen atom to which they are attached, may also form a heterocyclyl. Both the heterocyclyl for $R^2$ and the heterocyclyl formed together by $R^1$, $R^2$, and the nitrogen atom to which they are attached, may optionally be substituted by one or more substituents independently selected from the group consisting of $C_{1-6}$ alkyl, $C_{2-6}$ alkenyl, $C_{2-6}$ alkynyl, $C_{1-6}$ alkoxy, halogen, cyano, nitro, amino, mono- or di-$C_{1-6}$ alkyl substituted amino, hydroxy, hydroxy $C_{1-6}$ alkyl, aminocarbonyl, mono- or di-$C_{1-6}$ alkyl substituted aminocarbonyl, halo $C_{1-6}$ alkyl, $C_{1-6}$ alkylsulfonyl, $C_{1-6}$ alkylsulfinyl, $C_{1-6}$ alkylthio, amino $C_{1-6}$ alkyl, mono- or di-$C_{1-6}$ alkyl substituted amino $C_{1-6}$ alkyl, aminosulfonyl and mono- or di-$C_{1-6}$ alkyl substituted amino sulfonyl, wherein one or two carbon atoms of said heterocyclyl can optionally be replaced with a carbonyl group.

Intermediate II is coupled with 1-(ethoxycarbonylmethyl)-piperazine as described for the preparation of intermediate I in "1. Synthesis of thiazole derivatives: route A". Preferred conditions are DMF, BOP and DIPEA.

Alkaline hydrolysis of intermediate IV is effected as described for the preparation of intermediate II in "1. Synthesis of thiazole derivatives: route A". Preferred conditions are NaOH in $H_2O$/EtOH.

Intermediate V is coupled with a primary or secondary amine as described for the preparation of intermediate I in "1. Synthesis of thiazole derivatives: route A".

Preferred conditions are DMF, BOP and DIPEA or $CH_2Cl_2$, TBTU and TEA.

3. Synthesis of Thiazole Derivatives: Route C

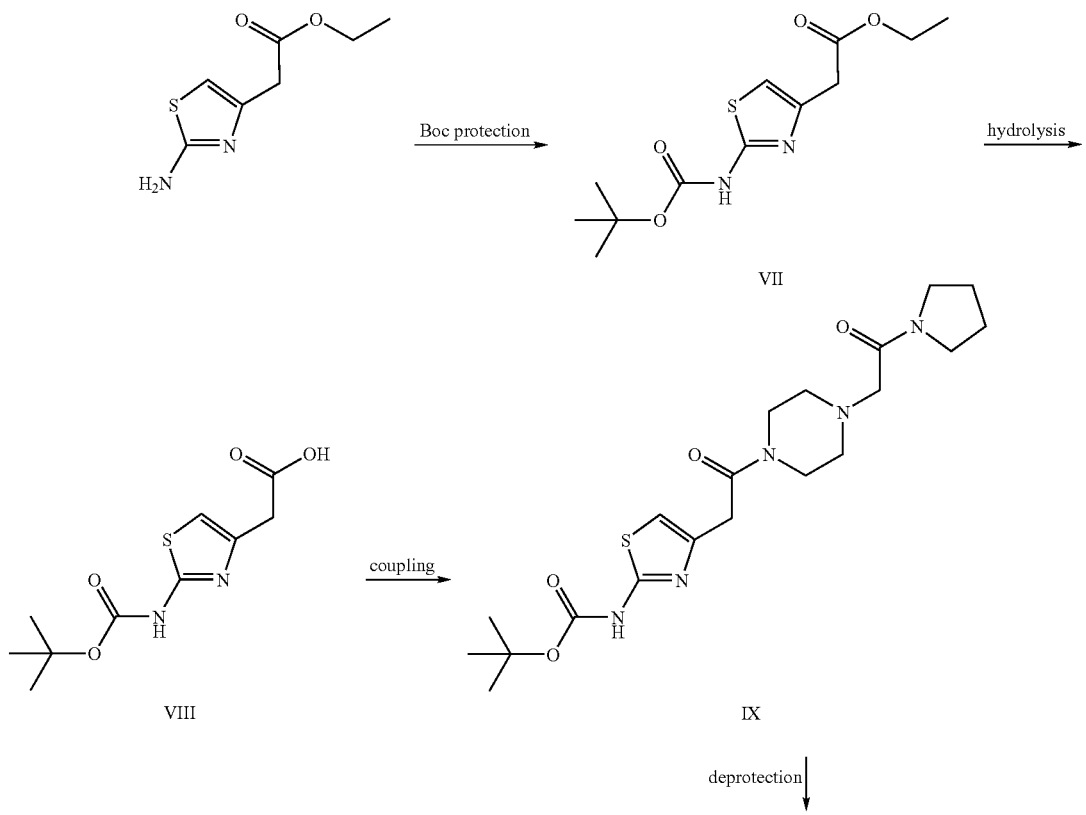

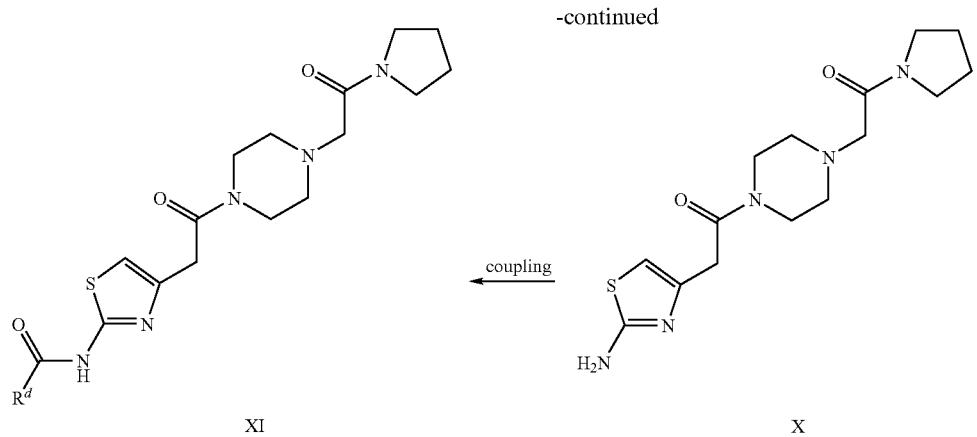

$R^d$ in the scheme is as defined before.

The starting 2-(2-aminothiazol-4-yl)-ethyl acetate is converted to the t-butyloxycarbonyl protected amine by reacting it with Boc$_2$O in a suitable solvent such as dichloromethane, acetonitrile, THF, or DMF. An additive such as a catalytic amount of DMAP may be added. The Boc-protected intermediate VII is obtained after reaction for 0.5-120 h at 0° C. to 50° C. Preferred conditions are CH$_2$Cl$_2$ and DMAP.

Alkaline hydrolysis of intermediate VII is effected as described for the preparation of intermediate II in "1. Synthesis of thiazole derivatives: route A". Preferred conditions are NaOH in H$_2$O/EtOH.

Intermediate VIII is coupled with 1-(pyrrolidinocarbonylmethyl)piperazine as described for the preparation of intermediate I in "1. Synthesis of thiazole derivatives: route A". Preferred conditions are CH$_2$Cl$_2$, TBTU and TEA.

Deprotection of intermediate IX is then effected by treatment with a mineral acid such as HCl, HBr, H$_2$SO$_4$ or H$_3$PO$_4$ or a carbonic acid, in a solvent such as CH$_2$Cl$_2$, dioxane or HOAc at 0 to 60° C. Preferred conditions are 4N HCl in dioxane.

Intermediate X is then coupled with an aryl carboxylic acid $R^d$—COOH as described for the preparation of intermediate I in "1. Synthesis of thiazole derivatives: route A". Preferred conditions are EDCI, DMAP and dichloromethane.

4. Synthesis of Thiazole Derivatives: Route D

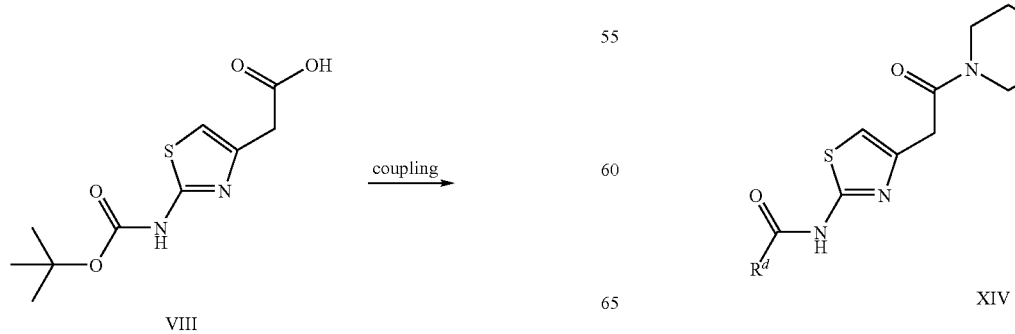

$R^d$ in the scheme is as defined before.

Intermediate VIII is coupled with 1-(N-methylpiperidin-4-yl)piperazine as described for the preparation of intermediate I in "1. Synthesis of thiazole derivatives: route A". Preferred conditions are DMF, BOP and DIPEA.

Deprotection of intermediate XII is then effected by treatment with a mineral acid such as HCl, HBr, $H_2SO_4$ or $H_3PO_4$ or a carbonic acid, in a solvent such as $CH_2Cl_2$, dioxane or HOAc at 0 to 60° C. Preferred conditions are HBr in HOAc.

Intermediate XIII is then coupled with an aryl carboxylic acid $R^d$—COOH as described for the preparation of intermediate I in "1. Synthesis of thiazole derivatives: route A". Preferred conditions are EDCI, DMAP and dichloromethane.

5. Synthesis of Thiazole Derivatives: Route E

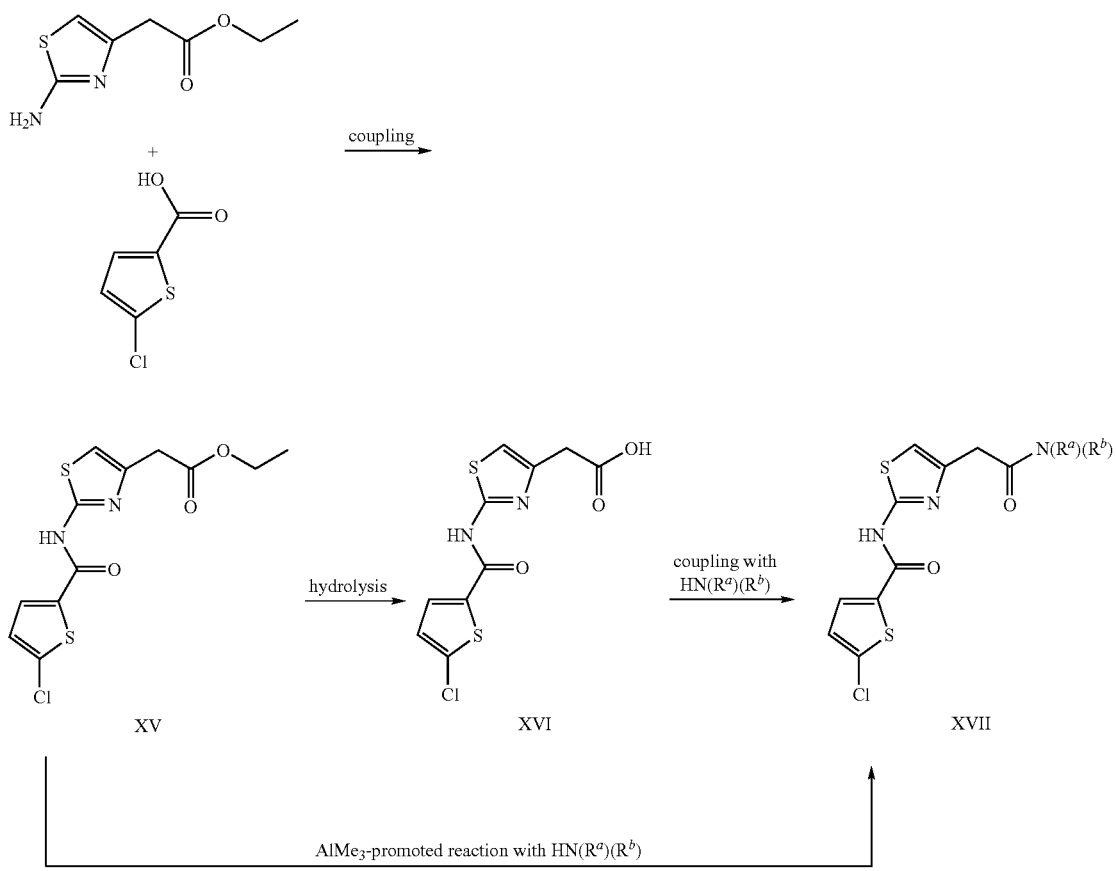

$R^a$ and $R^b$ in the scheme are as defined before.

The starting 5-chlorothiophene-2-carboxylic acid is coupled with 2-(2-aminothiazol-4-yl)-ethyl acetate as described for the preparation of intermediate I in "1. Synthesis of thiazole derivatives: route A". Preferred conditions are DMF, BOP and DIPEA.

Alkaline hydrolysis of intermediate XV is then effected as described for the preparation of intermediate II in "1. Synthesis of thiazole derivatives: route A". Preferred conditions are NaOH in $H_2O$/EtOH.

Intermediate XVI is coupled with an amine $HN(R^a)(R^b)$ as described for the preparation of intermediate I in "1. Synthesis of thiazole derivatives: route A". Preferred conditions are DMF, BOP and DIPEA.

Alternatively, intermediate XV can be directly reacted with an aniline $HN(R^a)(R^b)$. Anilines are preactivated with $AlMe_3$ in a solvent such as toluene or dioxane at r.t. and subsequently treated with ester XV at elevated temperature (usually 90° C.) to give the amide XVII.

6. Synthesis of Thiazole Derivatives: Route F
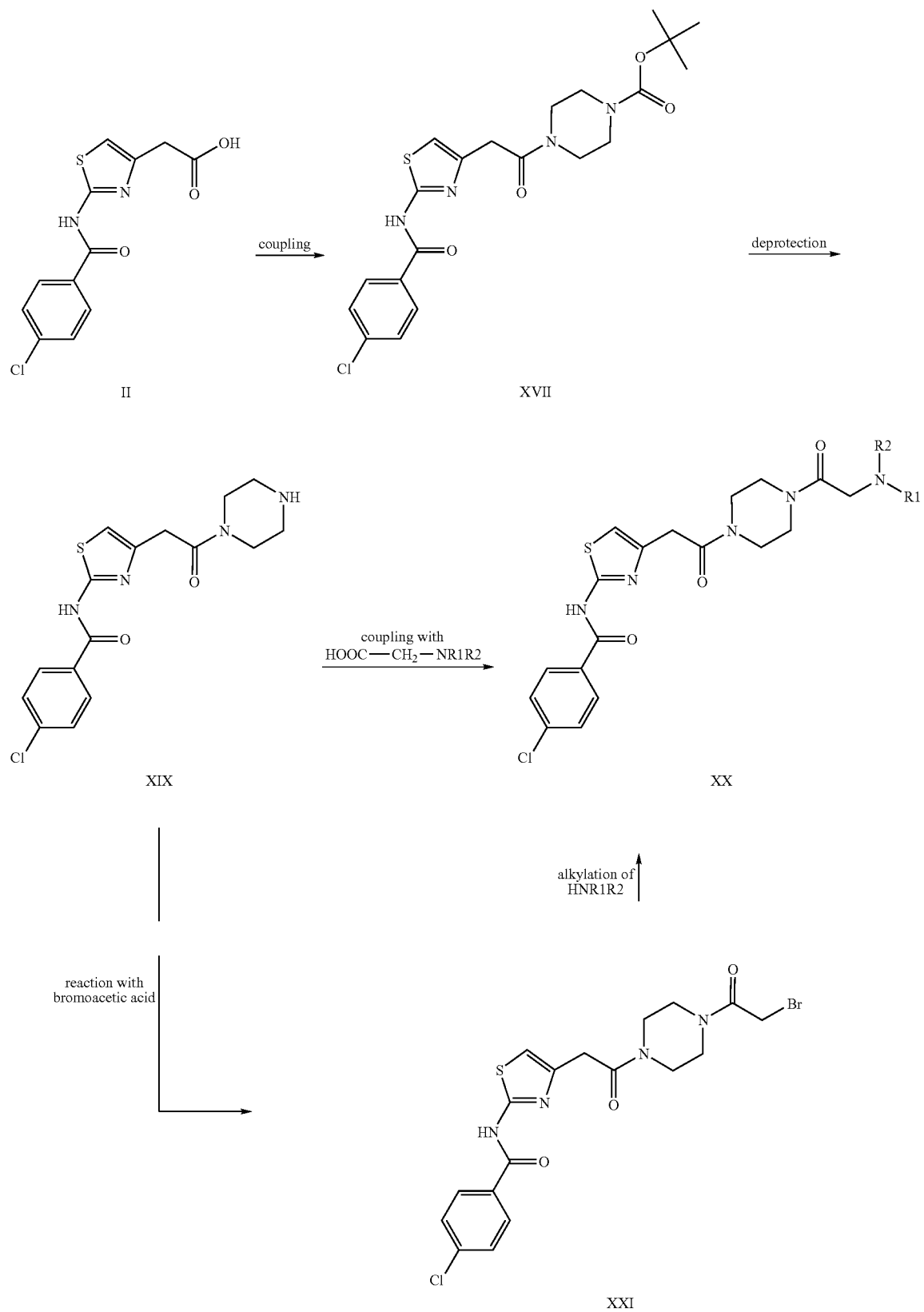

In the scheme shown above, $R^1$ is hydrogen, $C_{1-6}$ alkyl, $C_{2-6}$ alkenyl or $C_{2-6}$ alkynyl and $R^2$ is hydrogen, $C_{1-6}$ alkyl, $C_{2-6}$ alkenyl, $C_{2-6}$ alkynyl, $C_{3-7}$ cycloalkyl $C_{1-6}$ alkyl or heterocyclyl, provided that $R^2$ can be $C_{3-7}$ cycloalkyl $C_{1-6}$ alkyl or heterocyclyl, only when $R^1$ is hydrogen or $C_{1-6}$ alkyl. $R^1$ and $R^2$, together with the nitrogen atom to which they are attached, may also form a heterocyclyl. Both the heterocyclyl for $R^2$ and the heterocyclyl formed together by $R^1$, $R^2$, and the nitrogen atom to which they are attached, may optionally be substituted by one or more substituents independently selected from the group consisting of $C_{1-6}$ alkyl, $C_{2-6}$ alkenyl, $C_{2-6}$ alkynyl, $C_{1-6}$ alkoxy, halogen, cyano, nitro, amino, mono- or di-$C_{1-6}$ alkyl substituted amino, hydroxy, hydroxy $C_{1-6}$ alkyl, aminocarbonyl, mono- or di-$C_{1-6}$ alkyl substituted aminocarbonyl, halo $C_{1-6}$ alkyl, $C_{1-6}$ alkylsulfonyl, $C_{1-6}$ alkylsulfinyl, $C_{1-6}$ alkylthio, amino $C_{1-6}$ alkyl, mono- or di-$C_{1-6}$ alkyl substituted amino $C_{1-6}$ alkyl, aminosulfonyl and mono- or di-$C_{1-6}$ alkyl substituted amino sulfonyl, wherein one or two carbon atoms of said heterocyclyl can optionally be replaced with a carbonyl group.

Intermediate II is coupled with tert-butyl-1-piperazine carboxylate as described for the preparation of intermediate I in "1. Synthesis of thiazole derivatives: route A". Preferred conditions are DMF, BOP and DIPEA.

Deprotection of intermediate XVIII is then effected by treatment with a mineral acid such as HCl, HBr, $H_2SO_4$ or $H_3PO_4$ or a carbonic acid, in a solvent such as $CH_2Cl_2$, dioxane or HOAc at 0 to 60° C. Preferred conditions are 4N HCl in dioxane.

Intermediate XIX is coupled with glycine derivatives HOOC—$CH_2$—$NR^1R^2$ as described for the preparation of intermediate I in "1. Synthesis of thiazole derivatives: route A". Preferred conditions are DMF, BOP and DIPEA.

Alternatively intermediate XIX is coupled with bromo acetic acid as described for the preparation of intermediate I in "1. Synthesis of thiazole derivatives: route A". Preferred conditions are DMF, BOP and DIPEA. The resulting α-bromoacetic acid amide is then treated with an excess of a primary or secondary amine in a suitable solvent such as $CH_2Cl_2$, THF, acetonitrile etc. in the presence of an organic base such as TEA, DIPEA etc. and reacted for 0.5-120 h at −20° C. to 50° C.

7. Synthesis of Pyrazole, Triazole and Tetrazole Derivatives

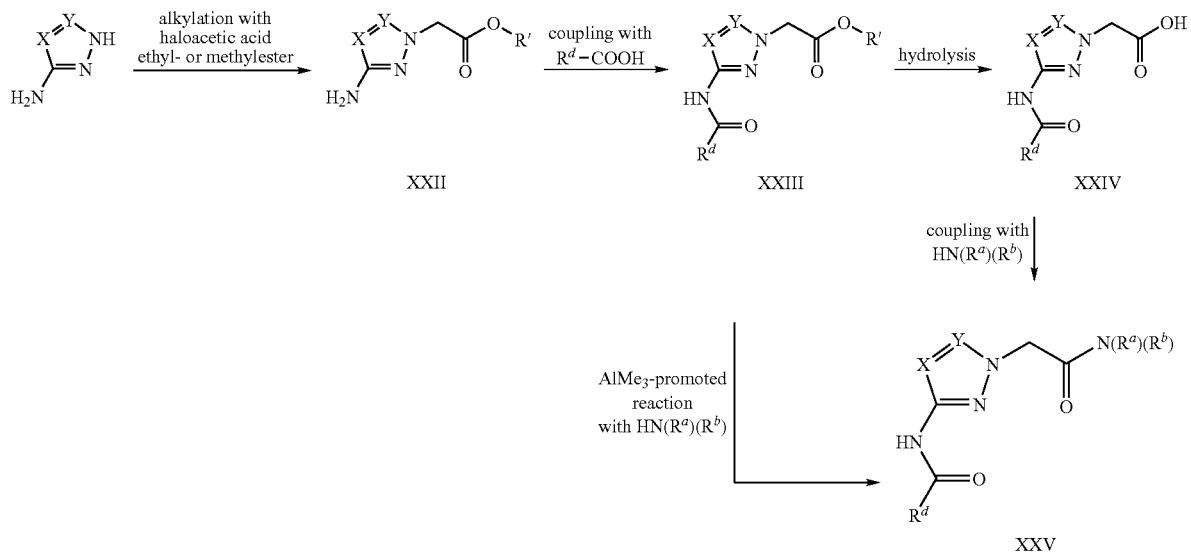

$R^a$, $R^b$ and $R^d$ in the scheme are as defined before. Both X and Y are CH or both X and Y are N or X is N and Y is CH, and R' is methyl or ethyl.

The starting heterocycle is deprotonated with a base such as NaH or KOtBu in a suitable solvent such as DMF. Alternatively, a combination of KOH in MeOH may be used. The anion is reacted with a suitable alkylating agent such as ethyl iodoacetate, ethyl bromoacetate or methyl chloroacetate for 0.5-120 h at 0° C. to 50° C.

Intermediate XXII is coupled with an aryl carboxylic acid $R^d$—COOH as described for the preparation of intermediate I in "1. Synthesis of thiazole derivatives: route A". Preferred conditions are dichloromethane, EDCI/DMAP and TEA.

Alkaline hydrolysis of intermediate XXIII is then effected as described for the preparation of intermediate II in "1. Synthesis of thiazole derivatives: route A". Preferred conditions are NaOH in $H_2O$/EtOH.

Intermediate XXIV is coupled with an amine $HN(R^a)(R^b)$ as described for the preparation of intermediate I in "1. Synthesis of thiazole derivatives: route A" to give amide XXV. Preferred conditions are DMF, BOP and DIPEA or MeCN, BOP-Cl and DIPEA.

Alternatively, intermediate XXIII can be directly reacted with an aniline $HN(R^a)(R^b)$. Anilines are preactivated with $AlMe_3$ in a solvent such as toluene or dioxane at r.t. and subsequently treated with ester XXIII at elevated temperature (usually 90° C.) to give the amide XXV.

8. Synthesis of Pyridone Derivatives

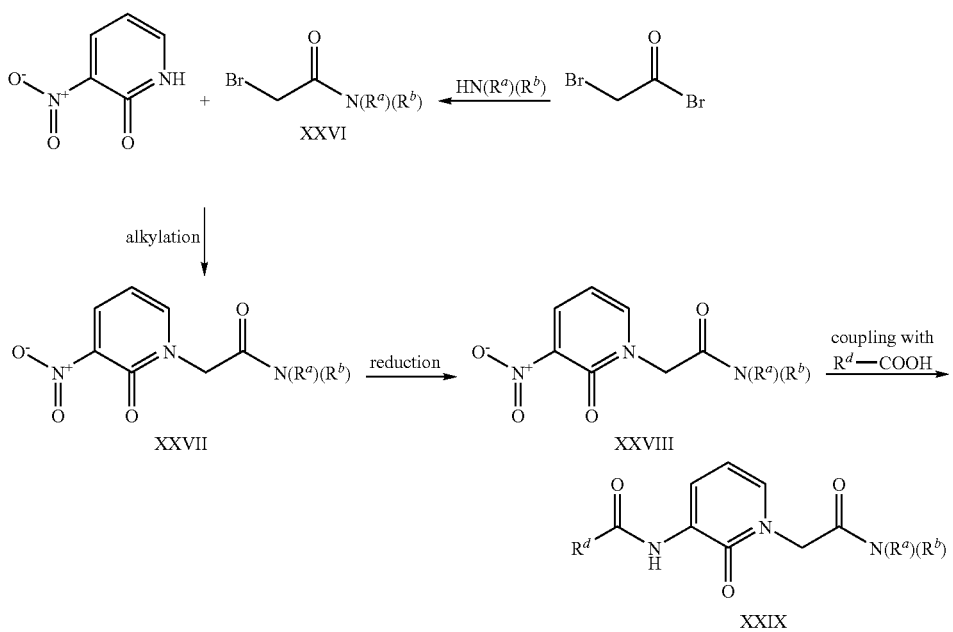

$R^a$, $R^b$ and $R^d$ in the scheme are as defined before.

Bromoacetic acid bromide is reacted with an amine $HN(R^a)(R^b)$ in a solvent such as THF, acetonitrile or $CH_2Cl_2$ in the presence of a organic base such as triethylamine or DIPEA for 0.5-120 h at 0° C. to 50° C.

3-Nitro-pyridone is deprotonated with a base such as NaH or KOtBu in a suitable solvent such as DMF. The anion is reacted with bromide XXVI for 0.5-120 h at 0° C. to 50° C. The nitro group of intermediate XXVII is then reduced, preferably with zinc in acetic acid. Intermediate XXVIII is coupled with an aryl acetic acid $R^d$—COOH as described for the preparation of intermediate I in "1. Synthesis of thiazole derivatives: route A". Preferred conditions are BOP, DIPEA and DMF.

As described above, the compounds of formula (I) are active compounds and inhibit the coagulation factor Xa. These compounds consequently influence both platelet activation which is induced by this factor and plasmatic blood coagulation. They therefore inhibit the formation of thrombi and can be used for the treatment and/or prevention of thrombotic disorders, such as, amongst others, arterial and venous thrombosis, deep vein thrombosis, peripheral arterial occlusive disease (PAOD), unstable angina pectoris, myocardial infarction, coronary artery disease, pulmonary embolism, stroke (cerebral thrombosis) due to atrial fibrillation, inflammation and arteriosclerosis. The compounds of the present invention can also be used in the treatment of acute vessel closure associated with thrombolytic therapy and restenosis, e.g. after transluminal coronary angioplasty (PTCA) or bypass grafting of the coronary or peripheral arteries and in the maintenance of vascular access patency in long term hemodialysis patients. F.Xa inhibitors of this invention may form part of a combination therapy with an anticoagulant with a different mode of action or with a platelet aggregation inhibitor or with a thrombolytic agent. Furthermore, these compounds have an effect on tumor cells and prevent metastases. They can therefore also be used as antitumor agents.

Prevention and/or treatment of thrombotic disorders, particularly arterial or deep vein thrombosis, is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of diseases which are associated with the coagulation factor Xa, particularly as therapeutically active substances for the treatment and/or prophylaxis of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumor.

In another preferred embodiment, the invention relates to a method for the therapeutic and/or prophylactic treatment of diseases which are associated with the coagulation factor Xa, particularly for the therapeutic and/or prophylactic treatment of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumor, which method comprises administering a compound as defined above to a human being or animal.

The inhibition of the coagulation factor Xa by the compounds of the present invention can be demonstrated with the aid of a chromogenic peptide substrate assay as described hereinafter.

The activity of the low molecular weight substances can, moreover, be characterized in the "prothrombin time" (PT) clotting test. The substances are prepared as a 10 mM solution in DMSO and thereafter made up to the desired dilution in the same solvent. Thereafter, 0.25 ml of human plasma (obtained from whole blood anticoagulated with ⅒ volume of 108 mM Na citrate) is placed in the instrument-specific sample container. In each case 5 μl of each dilution of the substance-dilution series is then mixed with the plasma provided. This plasma/inhibitor mixture is incubated at 37° C. for 2 minutes. Thereafter, 50 μl of plasma/inhibitor mixture is pipetted to the semi-automatic device (ACL, Automated Coagulation Laboratory (Instrument Laboratory)) into the measurement container. The clotting reaction is initiated by the addition of 0.1 ml of Dade® Innovin® (recombinant human tissue factor combined with calcium buffer and synthetic phospholipids, Dade Behring, Inc., Cat. B4212-50). The time up to the fibrin cross-linking is determined photooptically from the ACL. The inhibitor concentration, which brings about a doubling of the PT clotting time, is determined by fitting the data to an exponential regression (XLfit).

The compounds of the present invention can furthermore be characterised by the Activated Partial Thromboplastin Time (aPTT). This coagulation test can, e.g., be run on the ACL 300 Coagulation System (Instrumentation Laboratory) automatic analyzer. The substances are prepared as a 10 mM solution in DMSO and thereafter made up to the desired dilution in the same solvent. The test is performed with the Dade® Actin® FS Activated PTT reagent (purified soy phosphatides in $1.0 \times 10^{-4}$M ellagic acid, stabilizers and preservative, Dade Behring, Inc., Cat. B4218-100). Thereafter, 0.25 ml aliquots of human plasma (obtained from whole blood anticoagulated with 1/10 volume of 108 mM Na citrate) are spiked with 5 μl of test compound in at least 6 concentrations. 50 μl plasma at 4° C. containing 1/50 vol. inhibitor in solvent are incubated with 50 μl Dade® Actin® FS Activated PTT reagent in water at 37° C. for 3 min., then 50 μl CaCl2.2H2O 25 mM in water at 37° C. are added. The time up to the fibrin cross-linking is determined photooptically from the ACL. The inhibitor concentration, which brings about a doubling of the APTT clotting time, is determined by fitting the data to an exponential regression (XLfit).

The Ki values of the active compounds of the present invention are preferably between about 0.001 and about 50 μM, especially between about 0.001 and about 1 μM. The PT values are preferably between about 0.5 and about 100 μM, especially between about 0.5 and about 10 μM. The aPTT values are preferably between about 0.5 and about 100 μM, especially between about 0.5 and about 10 μM.

| Example | Ki [μM] factor Xa |
| --- | --- |
| Ex. 37.5 | 0.062 |
| Ex. 47.3 | 0.026 |
| Ex. 61.4 | 0.006 |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

The following Examples serve to illustrate the present invention in more detail. They are, however, not intended to limit its scope in any manner.

EXAMPLES

General Procedures

General Procedure A: Coupling of a Carboxylic Acid with an Amine Using Bop as a Coupling Reagent To a stirred solution of the acid (1 eq) in DMF is added the amine (1.2-2 eq), N-ethyl-diisopropylamine (3-4 eq) and then BOP-reagent (1.2-1.5 eq). The mixture is stirred at r.t. under an argon atmosphere for 3-24 h. The mixture is diluted with EtOAc, washed with water and brine, dried (MgSO$_4$), filtered and concentrated. The crude product can be purified by chromatography (silicagel) or by crystallization.

General Procedure B: Coupling of a Carboxylic Acid with an Amine Using BOP-Cl as a Coupling Reagent To a stirred solution of the acid (1 eq) in MeCN is added the amine (1.1 eq), N-ethyl-diisopropylamine (3 eq) and then BOP-Cl (1.05-2 eq). The mixture is stirred at r.t. under an argon atmosphere for 3-24 h. The mixture is diluted with EtOAc, washed with water and brine, dried (MgSO$_4$), filtered and concentrated. The crude product is purified by chromatography (silicagel).

General Procedure C: Coupling of a Carboxylic Acid with an Amine Using TBTU as a Coupling Reagent To a stirred solution of the acid (1 eq) in dichloromethane is added the amine (1.2 eq), triethylamine (2 eq) and then TBTU (1.2 eq). The mixture is stirred at r.t. under an argon atmosphere for 3-24 h. The mixture is diluted with dichloromethane, washed with saturated ammonium chloride solution, water and brine, dried (MgSO$_4$), filtered and concentrated. The crude product is purified by chromatography (silicagel).

General Procedure D: Coupling of a Carboxylic Acid with an Amine Using EDCI/DMAP as a Coupling Reagent To a stirred solution of the amine (1 eq) in dichloromethane/DMF 3:1 is added the acid (1.2 eq), triethylamine (2 eq), DMAP (0.5 eq) and then EDCI (2 eq). The mixture is then stirred at r.t. under an argon atmosphere for 24-96 h, then evaporated to dryness. The residue is taken up in 1N NaOH and washed with EtOAc. The aqueous phase is extracted several times with CH$_2$Cl$_2$/MeOH 9:1. The organic layer is dried (MgSO$_4$), filtered and concentrated. The crude product is purified by chromatography (silicagel).

General Procedure E: Hydrolysis of a Carboxylic Acid Ester to the Corresponding Carboxylic Acid The starting ester (1 eq) was dissolved in EtOH/H$_2$O 1:1 or MeOH/H$_2$O 1:1 to give a 5-10% solution which was treated at 0° C. with solid NaOH (3 eq). The reaction mixture was stirred at r.t. for 2-24 hrs. The EtOH was removed in the vacuum. The remaining aqueous solution was washed with diethyl ether, then acidified with 3N HCl. In some case the product precipitated upon acidification. In this case, the solid was filtered off and dried in the high vacuum. If no precipitation occurred, the acidic aqueous layer was extracted with EtOAc. The organic layer was washed with water and brine, then dried (MgSO$_4$). The product can be purified by crystallization of by chromatography (silicagel).

General Procedure F: Conversion of a Carboxylic Acid Ester to an Aryl Amide Using AlMe$_3$ Activation The starting aniline (1.2-4 eq) was dissolved in toluene or dioxane to give a 5-10% solution which was treated under an argon atmosphere at r.t. with AlMe$_3$ in heptane (1.2-4 eq). The reaction mixture was stirred at r.t. 90 min. Then the ester (1 eq) was added. The temperature was raised to 90°. Stirring was continued for 3-5 hrs. The reaction mixture was cooled to r.t., then concentrated. The residue was taken up in EtOAc and washed with 1N HCl. The organic layer was dried (MgSO4), filtered and concentrated. The product can be purified by crystallization or by chromatography (silicagel).

Example 1

1.1 Using general procedure A, 4-chlorobenzoic acid and 2-(2-aminothiazol-4-yl)-ethyl acetate were coupled to give [2-(4-chloro-benzoylamino)-thiazol-4-yl]-acetic acid ethyl ester. Light yellow solid. MS 325.3 ([M+H]$^+$)

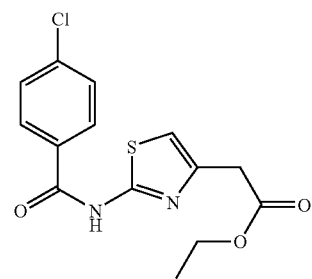

1.2 Using general procedure E, [2-(4-chloro-benzoylamino)-thiazol-4-yl]-acetic acid ethyl ester was hydrolyzed to give [2-(4-chloro-benzoylamino)-thiazol-4-yl]-acetic acid. Colorless solid. MS 295.5 ([M−H]$^−$)

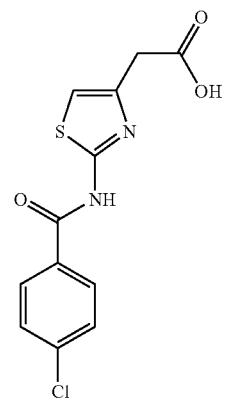

1.3 Using general method A, [2-(4-chloro-benzoylamino)-thiazol-4-yl]-acetic acid was coupled with 4-piperidino piperidine give to [4-(2-[1,4']-bipiperidinyl-1'-yl-2-oxo-ethyl)-thiazol-2-yl]-4-chloro-benzamide. Colorless solid. MS 447 ([M])

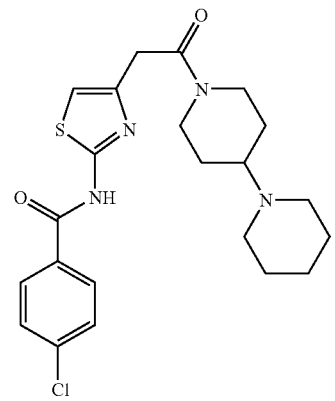

Example 2

In analogy to example 1.3, [2-(4-chloro-benzoylamino)-thiazol-4-yl]-acetic acid (example 1.2) was coupled with 1-benzyl-piperazine to give N-{4-[2-(4-benzyl-piperazin-1-yl)-2-oxo-ethyl]-thiazol-2-yl}-4-chloro-benzamide, using general method A. Orange solid. MS 455.4 ([M+H]$^+$)

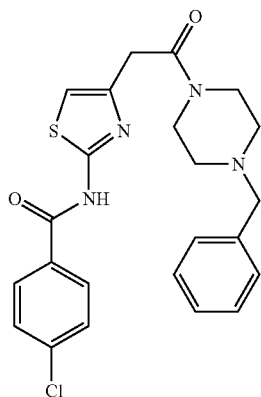

Example 3

In analogy to example 1.3, [2-(4-chloro-benzoylamino)-thiazol-4-yl]-acetic acid (example 1.2) was coupled with (1-cyclohexyl-methyl)piperazine to give 4-chloro-N-{4-[2-(4-cyclohexylmethyl-piperazin-1-yl)-2-oxo-ethyl]-thiazol-2-yl}-benzamide, using general procedure A. Colorless amorphous solid. MS 461.0 ([M+H]$^+$)

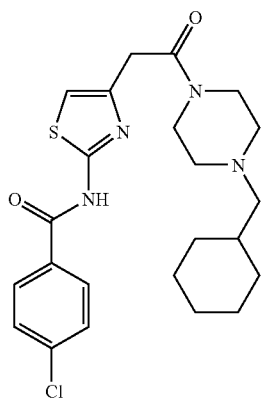

Example 4

In analogy to example 1.3, [2-(4-chloro-benzoylamino)-thiazol-4-yl]-acetic acid (example 1.2) was coupled with 1-(2-[4-morpholino]-ethyl)-piperazine to give 4-chloro-N-(4-{2-[4-(2-morpholin-4-yl-ethyl)-piperazin-1-yl]-2-oxo-ethyl}-thiazol-2-yl)-benzamide, using general procedure A. Colorless amorphous solid. MS 478.1 ([M+H]$^+$)

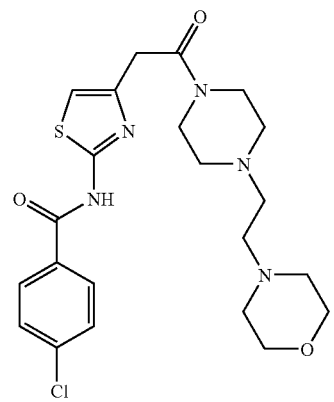

Example 5

In analogy to example 1.3, [2-(4-chloro-benzoylamino)-thiazol-4-yl]-acetic acid (example 1.2) was coupled with 1-(pyrrolidinocarbonylmethyl)piperazine to give 4-chloro-N-(4-{2-oxo-2-[4-(2-oxo-2-pyrrolidin-1-yl-ethyl)-piperazin-1-yl]-ethyl}-thiazol-2-yl)-benzamide, using general procedure A. Off-white solid. MS 476.1 ([M+H]$^+$)

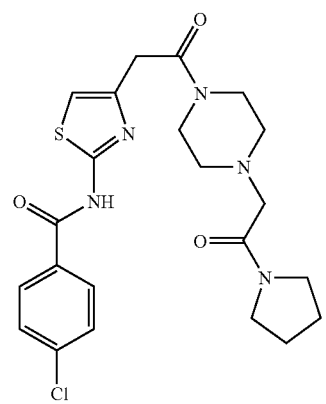

Example 6

In analogy to example 1.3, [2-(4-chloro-benzoylamino)-thiazol-4-yl]-acetic acid (example 1.2) was coupled with 1-cyclopentyl-piperazine to give 4-chloro-{4-[2-(4-cyclopentyl-piperazin-1-yl)-2-oxo-ethyl]-thiazol-2-yl}-benzamide, using general procedure A. Off-white solid. MS 433.3 ([M+H]$^+$)

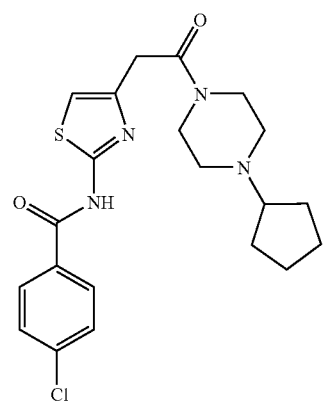

Example 7

In analogy to example 1.3, [2-(4-chloro-benzoylamino)-thiazol-4-yl]-acetic acid (example 1.2) was coupled with 1-(4-morpholido)-2-piperazinoethanone to give 4-chloro-N-(4-{2-[4-(2-morpholin-4-yl-2-oxo-ethyl)-piperazin-1-yl]-2-oxo-ethyl}-thiazol-2-yl)-benzamide, using general procedure A. Amorphous off-white solid. MS 492.3 ([M+H]$^+$)

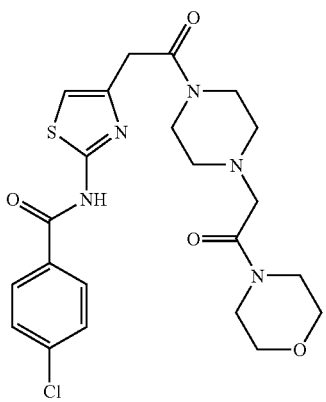

Example 8

In analogy to example 1.3, [2-(4-chloro-benzoylamino)-thiazol-4-yl]-acetic acid (example 1.2) was coupled with piperazino-acetic acid N,N-dimethylamide to give 4-chloro-N-{4-[2-(4-dimethylcarbamoylmethyl-piperazin-1-yl)-2-oxo-ethyl]-thiazol-2-yl}-benzamide, using general procedure A. Amorphous white solid. MS 450.0 ([M+H]$^+$)

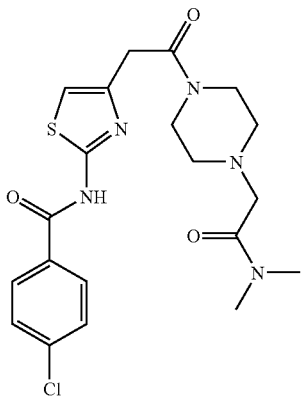

Example 9

In analogy to example 1.3, [2-(4-chloro-benzoylamino)-thiazol-4-yl]-acetic acid (example 1.2) was coupled with 1-(4-amino-3-fluoro-phenyl)-1H-pyridin-2-one (CAS 536747-52-1, prepared according to C. F. Bigge et al., patent application WO 2003045912) to give 4-chloro-N-(4-{[2-fluoro-4-(2-oxo-2H-pyridin-1-yl)-phenylcarbamoyl]-methyl}-thiazol-2-yl)-benzamide, using general procedure B. Off-white solid. MS 483.3 ([M+H]$^+$)

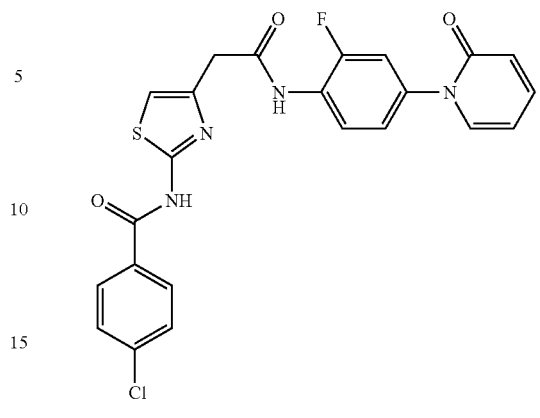

Example 10

In analogy to example 1.3, [2-(4-chloro-benzoylamino)-thiazol-4-yl]-acetic acid (example 1.2) was coupled with 4'-amino-3'-fluoro-biphenyl-2-sulfonic acid tert-butylamide (CAS 209919-51-7, prepared according to B.-Y. Zhu et al., patent application WO 2000071515) to give N-{4-[(2'-tert-butylsulfamoyl-3-fluoro-biphenyl-4-ylcarbamoyl)-methyl]-thiazol-2-yl}-4-chloro-benzamide, using general procedure C. White amorphous solid. MS 601.3 ([M+H]$^+$)

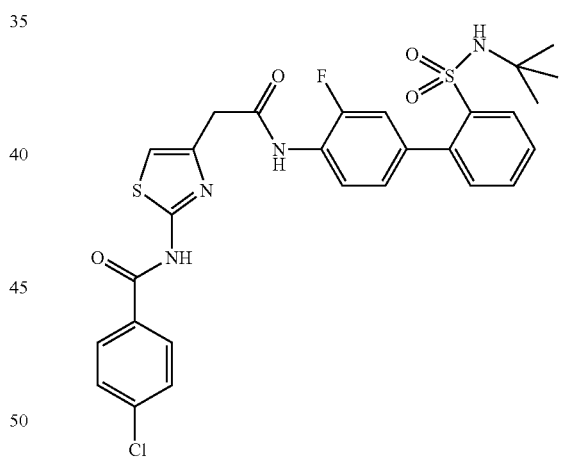

A solution of 163 mg N-{4-[(2'-tert-butylsulfamoyl-3-fluoro-biphenyl-4-ylcarbamoyl)-methyl]-thiazol-2-yl}-4-chloro-benzamide in 8 ml CHCl$_3$/MeOH 3:1 was cooled to −11° C. A stream of HCl gas was passed over the stirred solution for 10 min. The reaction mixture was kept at 4° C. over night, then concentrated. The crude product was purified by chromatography on silica using a gradient from CH$_2$Cl$_2$ to CH$_2$Cl$_2$/MeOH 9:1 in 20 minutes to give 112 mg 4-chloro-N-{4-[(3-fluoro-2'-sulfamoyl-biphenyl-4-ylcarbamoyl)-methyl]-thiazol-2-yl}-benzamide as white solid. MS 545.3 ([M+H]$^+$)

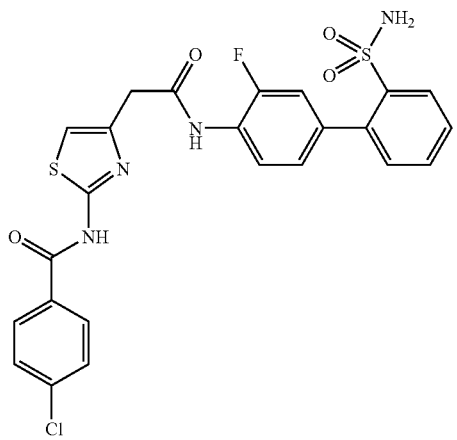

Example 11

In analogy to example 1.3, [2-(4-chloro-benzoylamino)-thiazol-4-yl]-acetic acid (example 1.2) was coupled with 1-(N-methylpiperidin-4-yl)piperazine to give 4-chloro-N-(4-{2-[4-(1-methyl-piperidin-4-yl)-piperazin-1-yl]-2-oxo-ethyl}-thiazol-2-yl)-benzamide, using general procedure C. Off-white solid. MS 462.3 ([M+H]$^+$)

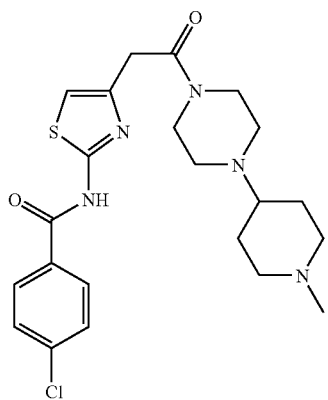

Example 12

In analogy to example 1.3, [2-(4-chloro-benzoylamino)-thiazol-4-yl]-acetic acid (example 1.2) was coupled with 5-(2-methanesulfonyl-phenyl)-pyridin-2-ylamine, hydrochloride (CAS 209959-31-9) to give 4-chloro-N-(4-{[5-(2-methanesulfonyl-phenyl)-pyridin-2-ylcarbamoyl]-methyl}-thiazol-2-yl)-benzamide, using general procedure C. White solid. MS 527.2 ([M+H]$^+$)

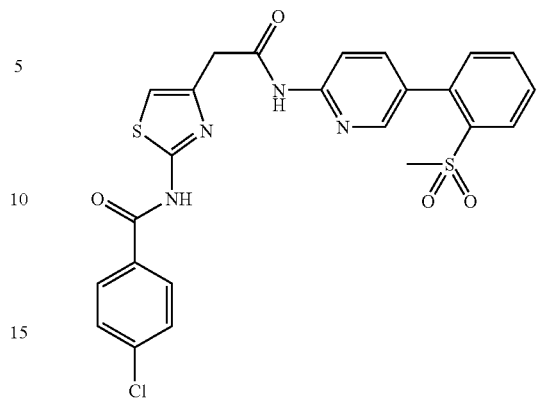

Example 13

In analogy to example 1.3, [2-(4-chloro-benzoylamino)-thiazol-4-yl]-acetic acid (example 1.2) was coupled with 3-[2-(1-piperazinyl)ethyl]-2-oxazolidinone hydrochloride (CAS 52548-39-7) to give 4-chloro-N-[4-(2-oxo-2-{4-[2-(2-oxo-oxazolidin-3-yl)-ethyl]-piperazin-1-yl}-ethyl)-thiazol-2-yl]-benzamide, using general procedure C. White amorphous solid. MS 478.4 ([M+H]$^+$)

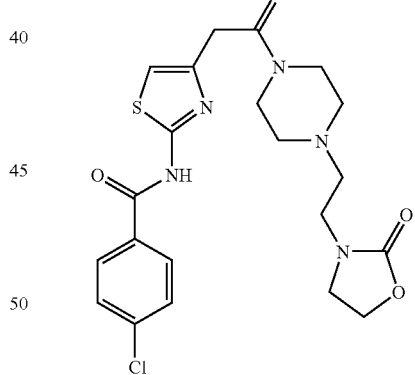

Example 14

In analogy to example 1.3, [2-(4-chloro-benzoylamino)-thiazol-4-yl]-acetic acid (example 1.2) was coupled with phenyl-piperazin-1-yl-methanone (CAS 13754-38-6) to give N-{4-[2-(4-benzoyl-piperazin-1-yl)-2-oxo-ethyl]-thiazol-2-yl}-4-chloro-benzamide, using general procedure C. White solid. MS 469.3 ([M+H]$^+$)

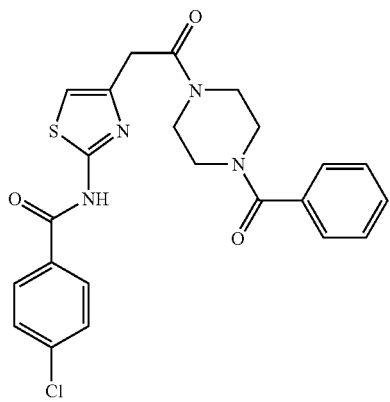

Example 15

In analogy to example 1.3, [2-(4-chloro-benzoylamino)-thiazol-4-yl]-acetic acid (example 1.2) was coupled with 2-(piperazino)-2-thiazoline dihydrochloride to give 4-chloro-N-(4-{2-[4-(4,5-dihydro-thiazol-2-yl)-piperazin-1-yl]-2-oxo-ethyl}-thiazol-2-yl)-benzamide, using general procedure C. White solid. MS 450.0 ([M+H]$^+$)

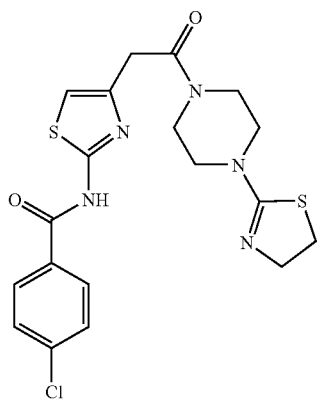

Example 16

In analogy to example 1.3, [2-(4-chloro-benzoylamino)-thiazol-4-yl]-acetic acid (example 1.2) was coupled with 2-(piperidin-4-yloxy)-pyridine dihydrochloride (CAS 313490-36-7) to give 4-chloro-N-(4-{2-oxo-2-[4-(pyridin-2-yloxy)-piperidin-1-yl]-ethyl}-thiazol-2-yl)-benzamide, using general procedure C. White amorphous solid. MS 457.6 ([M+H]$^+$)

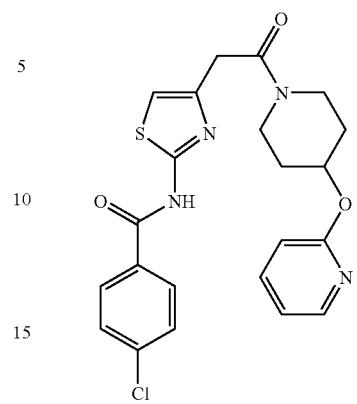

Example 17

In analogy to example 1.3, [2-(4-chloro-benzoylamino)-thiazol-4-yl]-acetic acid (example 1.2) was coupled with 4-(2-dimethylaminomethyl-imidazol-1-yl)-2-fluoro-phenylamine (CAS 218301-68-9, prepared according to U.S. Ser. No. 02/38168) to give 4-chloro-(4-{[4-(2-dimethylaminomethyl-imidazol-1-yl)-2-fluoro-phenylcarbamoyl]-methyl}-thiazol-2-yl)-benzamide, using general procedure A. Off-white solid. MS 511.4 ([M−H]$^-$)

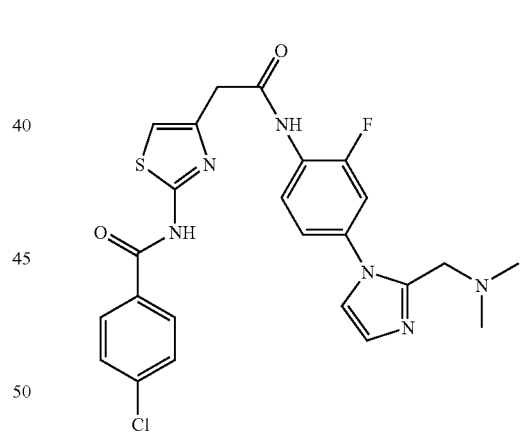

Example 18

In analogy to example 1.3, [2-(4-chloro-benzoylamino)-thiazol-4-yl]-acetic acid (example 1.2) was coupled with 4-(4-amino-3-fluoro-phenyl)-morpholin-3-one (CAS 742073-22-9) to give 4-chloro-(4-{[2-fluoro-4-(3-oxo-morpholin-4-yl)-phenylcarbamoyl]-methyl}-thiazol-2-yl)-benzamide, using general procedure A. Off-white solid. MS 489.3 ([M+H]$^+$)

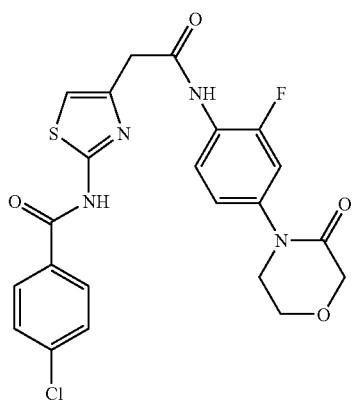

Example 19

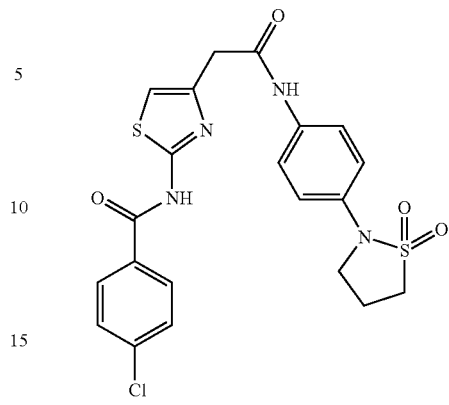

Example 21

In analogy to example 1.3, [2-(4-chloro-benzoylamino)-thiazol-4-yl]-acetic acid (example 1.2) was coupled with 4-(1,1-dioxo-[1,2]thiazinan-2-yl)-phenylamine hydrochloride (CAS 37441-49-9) to give 4-chloro-(4-{[4-(1,1-dioxo-[1,2]thiazinan-2-yl)-phenylcarbamoyl]-methyl}-thiazol-2-yl)-benzamide, using general procedure A. Yellow solid. MS 505.4 ([M+H]$^+$)

In analogy to example 1.3, [2-(4-chloro-benzoylamino)-thiazol-4-yl]-acetic acid (example 1.2) was coupled with 1-methyl-4-(piperidin-4-yl)-piperazine to give 4-chloro-(4-{2-[4-(4-methyl-piperazin-1-yl)-piperidin-1-yl]-2-oxo-ethyl}-thiazol-2-yl)-benzamide, using general procedure A. White solid. MS 462.4 ([M+H]$^+$)

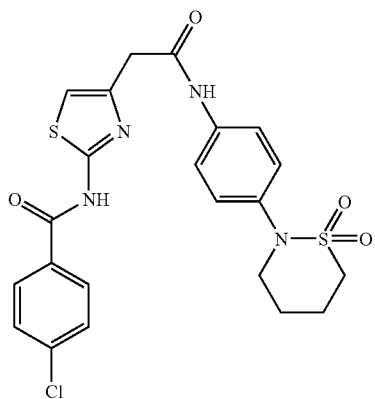

Example 20

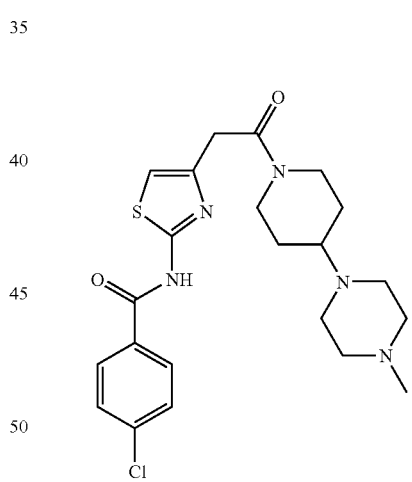

Example 22

In analogy to example 1.3, [2-(4-chloro-benzoylamino)-thiazol-4-yl]-acetic acid (example 1.2) was coupled with 4-(1,1-dioxo-isothiazolidin-2-yl)-phenylamine, hydrochlorid (CAS 90556-91-5) to give 4-chloro-(4-{[4-(1,1-dioxo-isothiazolidin-2-yl)-phenylcarbamoyl]-methyl}-thiazol-2-yl)-benzamide, using general procedure A. Light yellow solid. MS 491.3 ([M+H]$^+$)

22.1 Using general procedure A, [2-(4-chloro-benzoylamino)-thiazol-4-yl]-acetic acid (example 1.2) was coupled with 1-(ethoxycarbonylmethyl)-piperazine to give (4-{2-[2-(4-chloro-benzoylamino)-thiazol-4-yl]-acetyl}-piperazin-1-yl)-acetic acid ethyl ester. Off-white solid. MS 473.1 ([M+Na]$^+$)

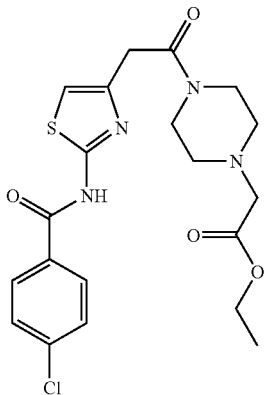

22.2 Using general procedure E, (4-{2-[2-(4-chloro-benzoylamino)-thiazol-4-yl]-acetyl}-piperazin-1-yl)-acetic acid ethyl ester was hydrolyzed to (4-{2-[2-(4-chloro-benzoylamino)-thiazol-4-yl]-acetyl}-piperazin-1-yl)-acetic acid. Off-white solid. MS 423.1 ([M+H]$^+$)

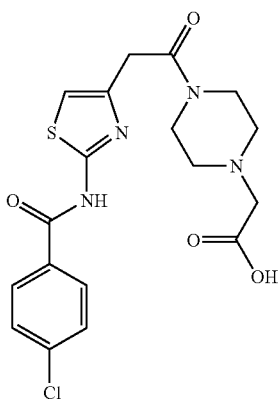

22.3 Using general procedure A, (4-{2-[2-(4-chloro-benzoylamino)-thiazol-4-yl]-acetyl}-piperazin-1-yl)-acetic acid was coupled with 1-methyl piperazine to give 4-chloro-N-[4-(2-{4-[2-(4-methyl-piperazin-1-yl)-2-oxo-ethyl]-piperazin-1-yl}-2-oxo-ethyl)-thiazol-2-yl]-benzamide. White solid. MS 505.3 ([M+H]$^+$)

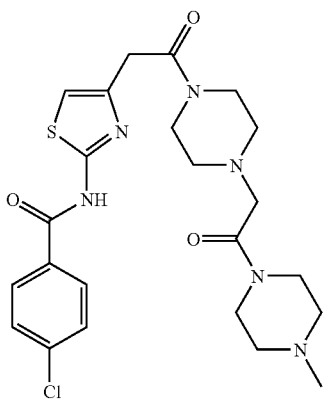

Example 23

In analogy to example 22.3, (4-{2-[2-(4-chloro-benzoylamino)-thiazol-4-yl]-acetyl}-piperazin-1-yl)-acetic acid (example 22.2) was coupled with 4-amino-1-methylpiperidine, using general method A, using THF instead of DMF as solvent, to give 4-chloro-N-[4-(2-{4-[(1-methyl-piperidin-4-ylcarbamoyl)-methyl]-piperazin-1-yl}-2-oxo-ethyl)-thiazol-2-yl]-benzamide. White solid. MS 519.3 ([M+H]$^+$)

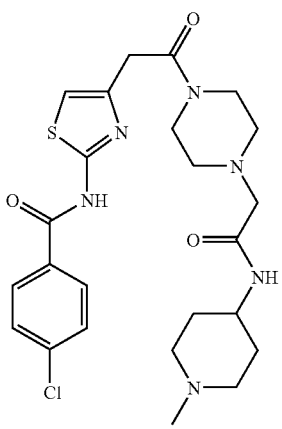

Example 24

In analogy to example 22.3, (4-{2-[2-(4-chloro-benzoylamino)-thiazol-4-yl]-acetyl}-piperazin-1-yl)-acetic acid (example 22.2) was coupled with 3-dimethylaminopyrrolidine, using general method A, using THF instead of DMF as solvent, to give 4-chloro-(RS)-[4-(2-{4-[2-(3-dimethylamino-pyrrolidin-1-yl)-2-oxo-ethyl]-piperazin-1-yl}-2-oxo-ethyl)-thiazol-2-yl]-benzamide. Off-white solid. MS 519.5 ([M])

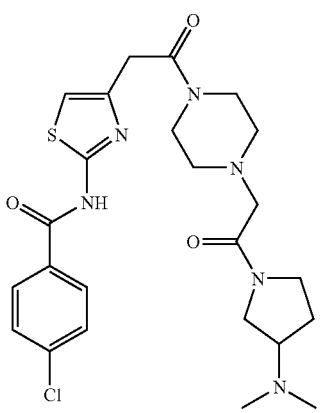

Example 25

In analogy to example 22.3, (4-{2-[2-(4-chloro-benzoylamino)-thiazol-4-yl]-acetyl}-piperazin-1-yl)-acetic acid (example 22.2) was coupled with 3-pyrrolidinol, using general method A, using THF instead of DMF as solvent, to give 4-chloro-(RS)-[4-(2-{4-[2-(3-hydroxy-pyrrolidin-1-yl)-2-oxo-ethyl]-piperazin-1-yl}-2-oxo-ethyl)-thiazol-2-yl]-benzamide. Off-white solid. MS 492.3 ([M])

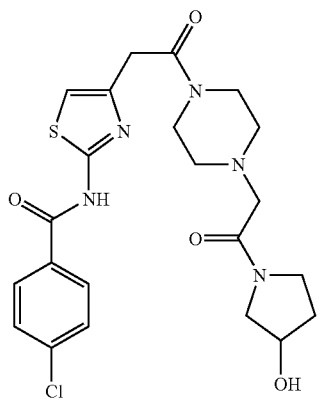

Example 26

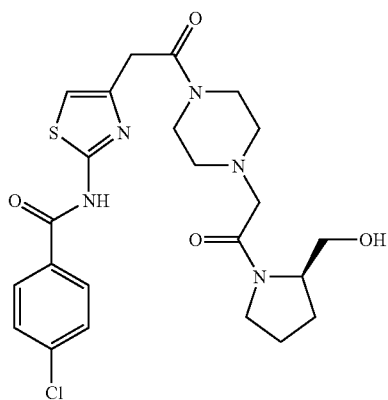

Example 27

In analogy to example 22.3, (4-{2-[2-(4-chloro-benzoylamino)-thiazol-4-yl]-acetyl}-piperazin-1-yl)-acetic acid (example 22.2) was coupled with (R)-(−)-2-(hydroxmethyl) pyrrolidine using general method A using THF instead of DMF as solvent to give 4-chloro-[4-(2-{4-[2-((R)-2-hydroxymethyl-pyrrolidin-1-yl)-2-oxo-ethyl]-piperazin-1-yl}-2-oxo-ethyl)-thiazol-2-yl]-benzamide. Off-white solid. MS 506.4 ([M])

In analogy to example 22.3, (4-{2-[2-(4-chloro-benzoylamino)-thiazol-4-yl]-acetyl}-piperazin-1-yl)-acetic acid (example 22.2) was coupled with (S)-(+)-2-(hydroxmethyl) pyrrolidine, using general method A, using THF instead of DMF as solvent, to give 4-chloro-[4-(2-{4-[2-((S)-2-hydroxymethyl-pyrrolidin-1-yl)-2-oxo-ethyl]-piperazin-1-yl}-2-oxo-ethyl)-thiazol-2-yl]-benzamide. Off-white solid. MS 506.4 ([M])

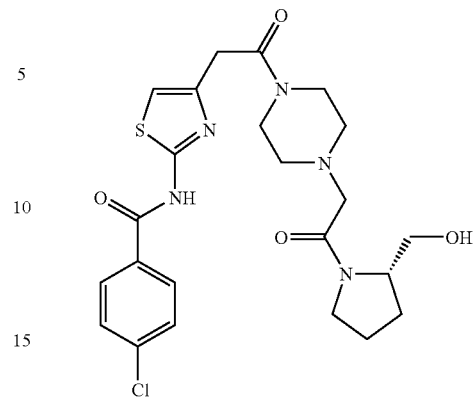

Example 28

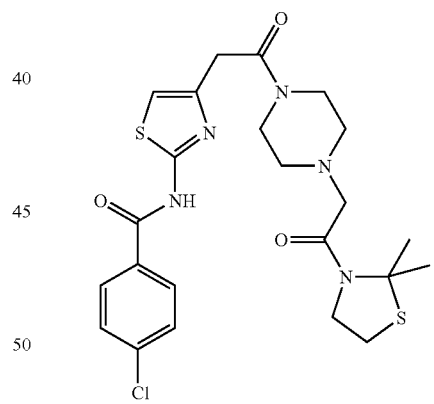

Example 29

In analogy to example 22.3, (4-{2-[2-(4-chloro-benzoylamino)-thiazol-4-yl]-acetyl}-piperazin-1-yl)-acetic acid (example 22.2) was coupled with 2,2-dimethylthiazolidine, using general method A, using THF instead of DMF as solvent, to give 4-chloro-[4-(2-{4-[2-(2,2-dimethyl-thiazolidin-3-yl)-2-oxo-ethyl]-piperazin-1-yl}-2-oxo-ethyl)-thiazol-2-yl]-benzamide. White solid. MS 522.0 ([M])

In analogy to example 22.3, (4-{2-[2-(4-chloro-benzoylamino)-thiazol-4-yl]-acetyl}-piperazin-1-yl)-acetic acid (example 22.2) was coupled with H-Pro-NMe$_2$, using general method C, to give (S)-1-[2-(4-{2-[2-(4-chloro-benzoylamino)-thiazol-4-yl]-piperazin-1-yl)-acetyl]-pyrrolidine-2-carboxylic acid dimethylamide. Off-white solid. MS 547.5 ([M+H]$^+$)

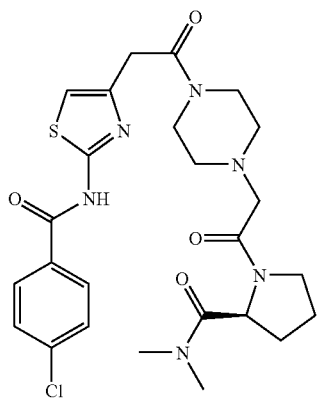

Example 30

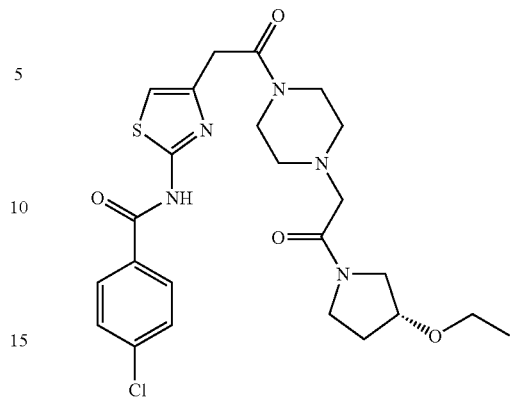

Example 32

In analogy to example 22.3, (4-{2-[2-(4-chloro-benzoylamino)-thiazol-4-yl]-acetyl}-piperazin-1-yl)-acetic acid (example 22.2) was coupled with nortropine, using general method C, to give 4-chloro-[4-(2-{4-[2-((1S,3R,5R)-3-hydroxy-8-aza-bicyclo[3.2.1]oct-8-yl)-2-oxo-ethyl]-piperazin-1-yl}-2-oxo-ethyl)-thiazol-2-yl]-benzamide. White solid. MS 532.3 ([M+H]$^+$)

In analogy to example 22.3, (4-{2-[2-(4-chloro-benzoylamino)-thiazol-4-yl]-acetyl}-piperazin-1-yl)-acetic acid (example 22.2) was coupled with thiazolidine, using general method C, with PyBOP instead of TBTU as coupling reagent, to give 4-chloro-(4-{2-oxo-2-[4-(2-oxo-2-thiazolidin-3-yl-ethyl)-piperazin-1-yl]-ethyl}-thiazol-2-yl)-benzamide. Light yellow solid. MS 494.4 ([M+H]$^+$)

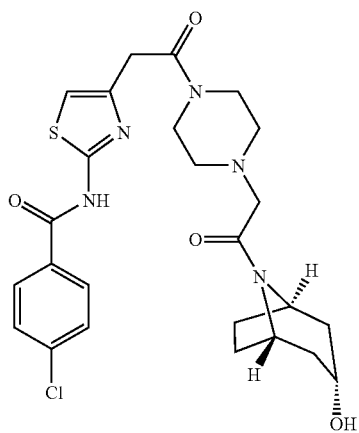

Example 31

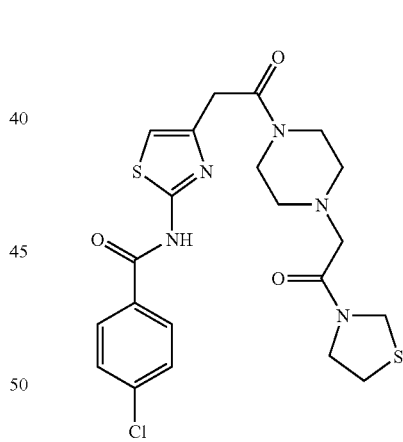

Example 33

In analogy to example 22.3, (4-{2-[2-(4-chloro-benzoylamino)-thiazol-4-yl]-acetyl}-piperazin-1-yl)-acetic acid (example 22.2) was coupled with (R)-3-ethoxy pyrrolidine, using general method C, to give 4-chloro-[4-(2-{4-[2-((R)-3-ethoxy-pyrrolidin-1-yl)-2-oxo-ethyl]-piperazin-1-yl}-2-oxo-ethyl)-thiazol-2-yl]-benzamide. Light yellow solid. MS 542.2 ([M+Na]$^+$)

In analogy to example 22.3, (4-{2-[2-(4-chloro-benzoylamino)-thiazol-4-yl]-acetyl}-piperazin-1-yl)-acetic acid (example 22.2) was coupled with 3-(tert-butyloxycarbonylamino)pyrrolidine, using general method C, to give {1-[2-(4-{2-[2-(4-chloro-benzoylamino)-thiazol-4-yl]-acetyl}-piperazin-1-yl)-acetyl]-pyrrolidin-3-yl}-carbamic acid tert-butyl ester. Off-white solid. MS 591.3 ([M+H]$^+$)

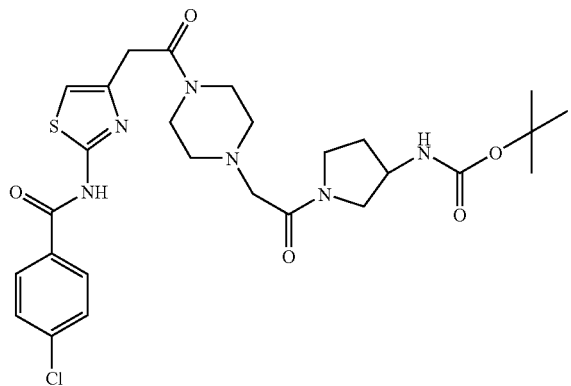

A solution of 180 mg {1-[2-(4-{2-[2-(4-chloro-benzoylamino)-thiazol-4-yl]-acetyl}-piperazin-1-yl)-acetyl]-pyrrolidin-3-yl}-carbamic acid tert-butyl ester in 2 ml MeOH was cooled to 0° C., then treated with 1.5 ml 4M HCl in dioxane. The reaction mixture was stirred over night at r.t., then concentrated. The residue was taken up in 5 ml 1N aqueous HCl and washed with diethylether. The aqueous layer was brought to pH 12 with 4N NaOH and extracted with EtOAc, then with CH$_2$Cl$_2$/MeOH 9:1. The combined organic layers were washed with brine, dried (MgSO$_4$), filtered and concentrated. The crude product was purified by chromatography on silica using a gradient from CH$_2$Cl$_2$ to CH$_2$Cl$_2$/MeOH 85:15 in 20 min to give 25 mg [4-(2-{4-[2-(3-amino-pyrrolidin-1-yl)-2-oxo-ethyl]-piperazin-1-yl}-2-oxo-ethyl)-thiazol-2-yl]-4-chloro-benzamide as light yellow solid. MS 491.5 ([M+H]$^+$)

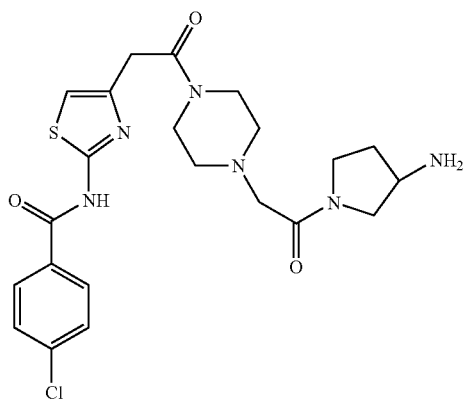

Example 34

In analogy to example 22.3, (4-{2-[2-(4-chloro-benzoylamino)-thiazol-4-yl]-acetyl}-piperazin-1-yl)-acetic acid (example 22.2) was coupled with (S)-2-(trifluoromethyl)pyrrolidine, using general method C, to give 4-chloro-[4-(2-oxo-2-{4-[2-oxo-2-((R)-2-trifluoromethyl-pyrrolidin-1-yl)-ethyl]-piperazin-1-yl}-ethyl)-thiazol-2-yl]-benzamide. White solid. MS 543.8 ([M+H]$^+$)

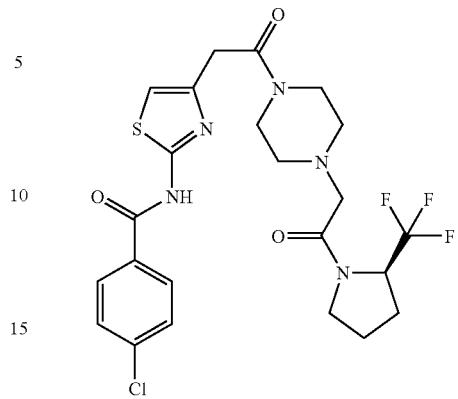

Example 35

In analogy to example 22.3, (4-{2-[2-(4-chloro-benzoylamino)-thiazol-4-yl]-acetyl}-piperazin-1-yl)-acetic acid (example 22.2) was coupled with H-Pro-NHMe, using general method C, to give (S)-1-[2-(4-{2-[2-(4-chloro-benzoylamino)-thiazol-4-yl]-acetyl}-piperazin-1-yl)-acetyl]-pyrrolidine-2-carboxylic acid methylamide. White solid. MS 533.3 ([M+H]$^+$)

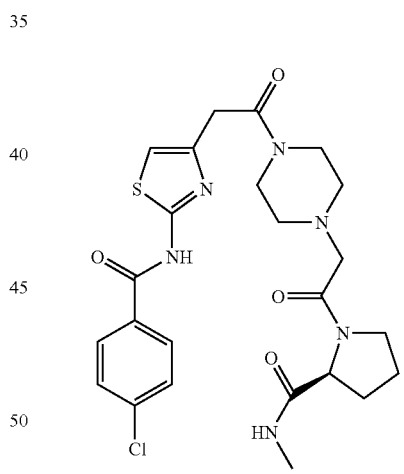

Example 36

In analogy to example 22.3, (4-{2-[2-(4-chloro-benzoylamino)-thiazol-4-yl]-acetyl}-piperazin-1-yl)-acetic acid (example 22.2) was coupled with (RS)-3-(methylsulfonyl) pyrrolidine, using general method C, to give 4-chloro-(RS)-[4-(2-{4-[2-(3-methanesulfonyl-pyrrolidin-1-yl)-2-oxo-ethyl]-piperazin-1-yl}-2-oxo-ethyl)-thiazol-2-yl]-benzamide. Off-white solid. MS 554.2 ([M+H]$^+$)

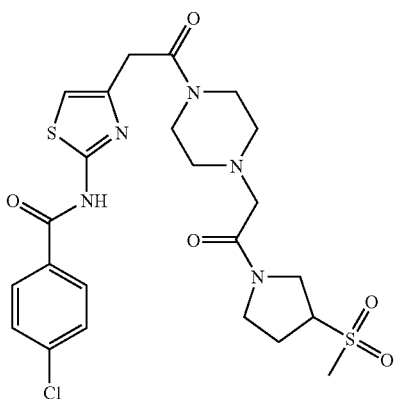

Example 37

37.1 A solution of 30 g 2-(2-aminothiazol-4-yl)-ethyl acetate in 200 ml CH$_2$Cl$_2$ was treated at 0° C. with 2.9 g DMAP under an argon atmosphere. A solution of 38.9 g Boc$_2$O in 50 ml CH$_2$Cl$_2$ was then added dropwise for 30 min. The resulting suspension was stirred at r.t. overnight. The reaction mixture was then washed with 5% aq. KHCO$_3$, H$_2$O, sat. aq. NH$_4$Cl and brine, dried (MgSO$_4$), filtered and concentrated to leave the crude product as a brown viscous oil. The product was isolated by chromatography on silica using EtOAc/cyclohexane 1:2 to give 40.5 g (2-tert-butoxycarbonylamino-thiazol-4-yl)-acetic acid ethyl ester as orange viscous oil. MS 287.0 ([M+H]$^+$)

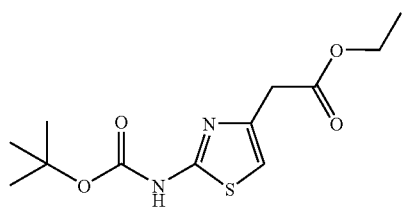

37.2 Using general procedure E, (2-tert-butoxycarbonylamino-thiazol-4-yl)-acetic acid ethyl ester was hydrolyzed to (2-tert-butoxycarbonylamino-thiazol-4-yl)-acetic acid. Colorless crystalline solid. MS 259.0 ([M+H]$^+$)

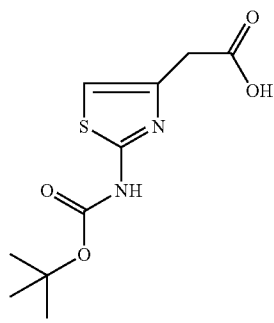

37.3 Using general procedure C, (2-tert-butoxycarbonylamino-thiazol-4-yl)-acetic acid was coupled with 1-(pyrrolidinocarbonylmethyl)piperazine to give (4-{2-oxo-2-[4-(2-oxo-2-pyrrolidin-1-yl-ethyl)-piperazin-1-yl]-ethyl}-thiazol-2-yl)-carbamic acid tert-butyl ester. White solid. MS 460.4 ([M+Na]$^+$)

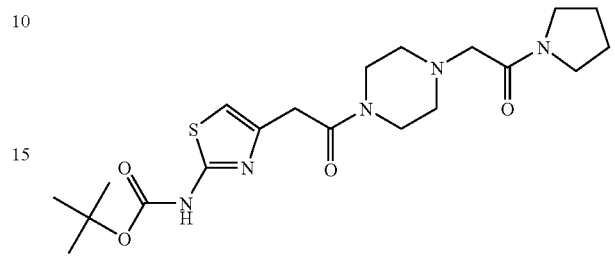

37.4 In analogy to example 33, (4-{2-oxo-2-[4-(2-oxo-2-pyrrolidin-1-yl-ethyl)-piperazin-1-yl]-ethyl}-thiazol-2-yl)-carbamic acid tert-butyl ester was deprotected to give 2-(2-amino-thiazol-4-yl)-1-[4-(2-oxo-2-pyrrolidin-1-yl-ethyl)-piperazin-1-yl]-ethanone. Off-white amorphous solid. MS 338.3 ([M+H]$^+$)

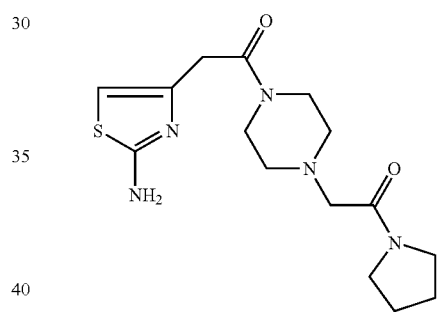

37.5 Using general procedure D, 2-(2-amino-thiazol-4-yl)-1-[4-(2-oxo-2-pyrrolidin-1-yl-ethyl)-piperazin-1-yl]-ethanone was coupled with 5-chlorothiophene-2-carboxylic acid to give 5-chloro-thiophene-2-carboxylic acid (4-{2-oxo-2-[4-(2-oxo-2-pyrrolidin-1-yl-ethyl)-piperazin-1-yl]-ethyl}-thiazol-2-yl)-amide. Light yellow amorphous solid. MS 482.4 ([M+H]$^+$)

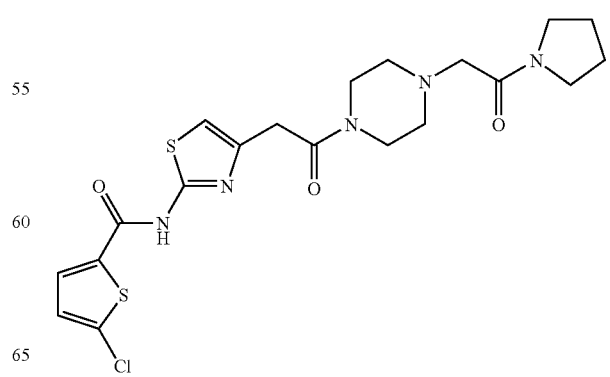

Example 38

In analogy to example 37.5, 2-(2-amino-thiazol-4-yl)-1-[4-(2-oxo-2-pyrrolidin-1-yl-ethyl)-piperazin-1-yl]-ethanone (example 37.4) was coupled with 5-bromothiophene-2-carboxylic acid, using general method D, to give 5-bromo-thiophene-2-carboxylic acid (4-{2-oxo-2-[4-(2-oxo-2-pyrrolidin-1-yl-ethyl)-piperazin-1-yl]-ethyl}-thiazol-2-yl)-amide. Light yellow solid. MS 528.1 ([M+H]$^+$)

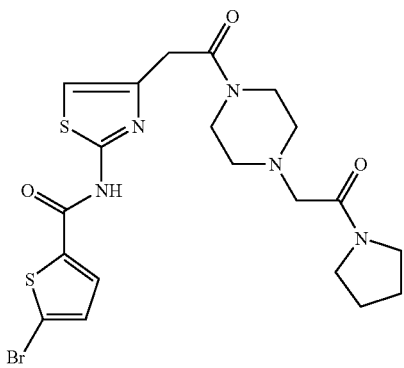

Example 39

In analogy to example 37.5, 2-(2-amino-thiazol-4-yl)-1-[4-(2-oxo-2-pyrrolidin-1-yl-ethyl)-piperazin-1-yl]-ethanone (example 37.4) was coupled with 5-methylthiophene-2-carboxylic acid, using general method D, to give 5-methyl-thiophene-2-carboxylic acid (4-{2-oxo-2-[4-(2-oxo-2-pyrrolidin-1-yl-ethyl)-piperazin-1-yl]-ethyl}-thiazol-2-yl)-amide. Light yellow solid. MS 462.3 ([M+H]$^+$)

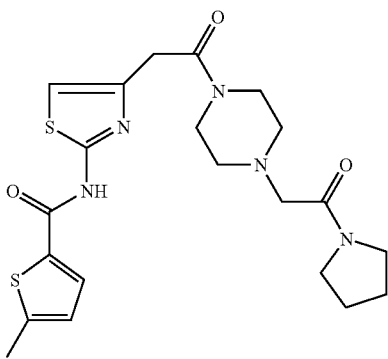

Example 40

In analogy to example 37.5, 2-(2-amino-thiazol-4-yl)-1-[4-(2-oxo-2-pyrrolidin-1-yl-ethyl)-piperazin-1-yl]-ethanone (example 37.4) was coupled with piperonylic acid, using general method D, to give benzo[1,3]dioxole-5-carboxylic acid (4-{2-oxo-2-[4-(2-oxo-2-pyrrolidin-1-yl-ethyl)-piperazin-1-yl]-ethyl}-thiazol-2-yl)-amide. Off-white solid. MS 486.4 ([M+H]$^+$)

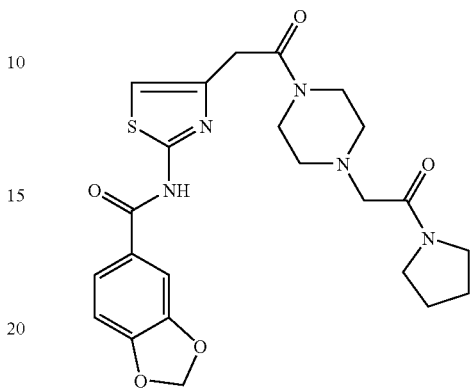

Example 41

In analogy to example 37.5, 2-(2-amino-thiazol-4-yl)-1-[4-(2-oxo-2-pyrrolidin-1-yl-ethyl)-piperazin-1-yl]-ethanone (example 37.4) was coupled with indole-6-carboxylic acid, using general method D, to give 1H-indole-6-carboxylic acid (4-{2-oxo-2-[4-(2-oxo-2-pyrrolidin-1-yl-ethyl)-piperazin-1-yl]-ethyl}-thiazol-2-yl)-amide. Off-white solid. MS 481.5 ([M+H]$^+$)

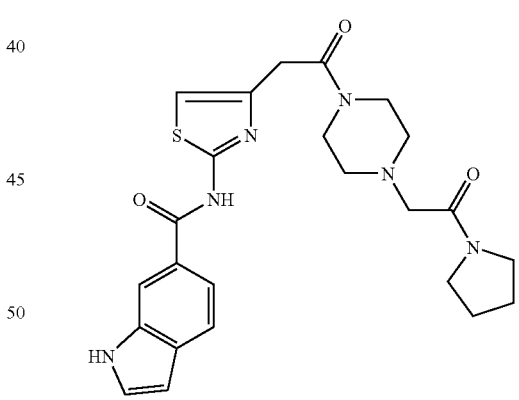

Example 42

In analogy to example 37.5, 2-(2-amino-thiazol-4-yl)-1-[4-(2-oxo-2-pyrrolidin-1-yl-ethyl)-piperazin-1-yl]-ethanone (example 37.4) was coupled with 4-chloro-3-fluorocarboxylic acid, using general method D, to give 4-chloro-3-fluoro-N-(4-{2-oxo-2-[4-(2-oxo-2-pyrrolidin-1-yl-ethyl)-piperazin-1-yl]-ethyl}-thiazol-2-yl)-benzamide. Off-white solid. MS 494.5 ([M+H]$^+$)

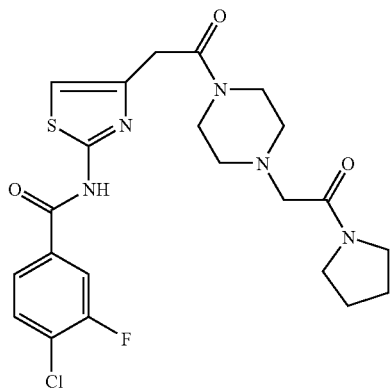

Example 43

In analogy to example 37.5, 2-(2-amino-thiazol-4-yl)-1-[4-(2-oxo-2-pyrrolidin-1-yl-ethyl)-piperazin-1-yl]-ethanone (example 37.4) was coupled with 3-fluoro-4-methoxycarboxylic acid, using general method D, to give 3-fluoro-4-methoxy-(4-{2-oxo-2-[4-(2-oxo-2-pyrrolidin-1-yl-ethyl)-piperazin-1-yl]-ethyl}-thiazol-2-yl)-benzamide. Light yellow solid. MS 490.4 ([M+H]+)

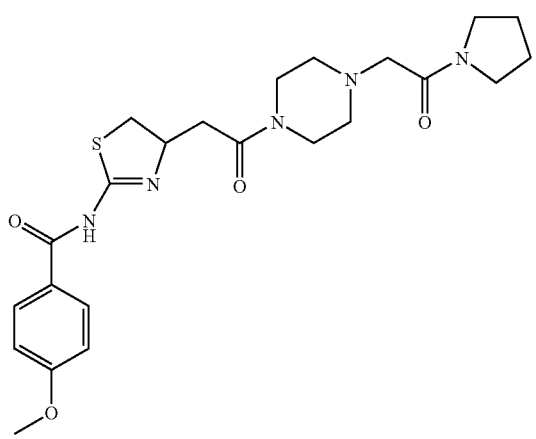

Example 44

In analogy to example 37.5, 2-(2-amino-thiazol-4-yl)-1-[4-(2-oxo-2-pyrrolidin-1-yl-ethyl)-piperazin-1-yl]-ethanone (example 37.4) was coupled with p-anisic acid, using general method D, to give 4-methoxy-(4-{2-oxo-2-[4-(2-oxo-2-pyrrolidin-1-yl-ethyl)-piperazin-1-yl]-ethyl}-thiazol-2-yl)-benzamide. White solid. MS 472.3 ([M+H]+)

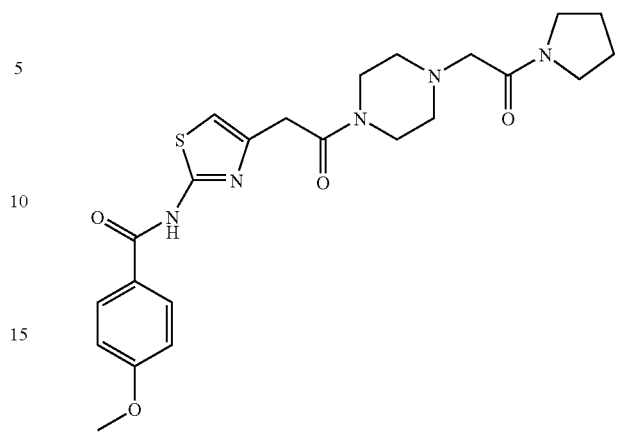

Example 45

In analogy to example 37.5, 2-(2-amino-thiazol-4-yl)-1-[4-(2-oxo-2-pyrrolidin-1-yl-ethyl)-piperazin-1-yl]-ethanone (example 37.4) was coupled with 5-chloro-pyridine-2-carboxylic acid, using general method D, to give 5-chloro-pyridine-2-carboxylic acid (4-{2-oxo-2-[4-(2-oxo-2-pyrrolidin-1-yl-ethyl)-piperazin-1-yl]-ethyl}-thiazol-2-yl)-amide. Yellow solid. MS 477.3 ([M+H]+)

Example 46

In analogy to example 37.5, 2-(2-amino-thiazol-4-yl)-1-[4-(2-oxo-2-pyrrolidin-1-yl-ethyl)-piperazin-1-yl]-ethanone (example 37.4) was coupled with 2,3-dihydrobenzofurane-5-carboxylic acid, using general method D, to give 2,3-dihydrobenzofuran-5-carboxylic acid (4-{2-oxo-2-[4-(2-oxo-2-pyrrolidin-1-yl-ethyl)-piperazin-1-yl]-ethyl}-thiazol-2-yl)-amide. White solid. MS 506.5 ([M+Na]+)

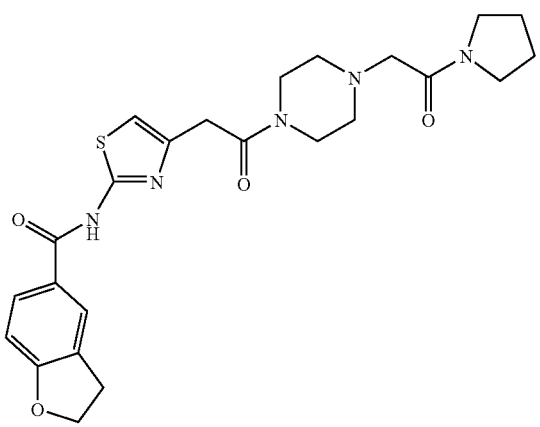

Example 47

47.1 Using general method C, (2-tert-butoxycarbonylamino-thiazol-4-yl)-acetic acid (example 37.2) was coupled with 1-(N-methylpiperidin-4-yl)piperazine to give (4-{2-[4-(1-methyl-piperidin-4-yl)-piperazin-1-yl]-2-oxo-ethyl}-thiazol-2-yl)-carbamic acid tert-butyl ester. Off-white powder. MS 424.0 ([M+H]$^+$)

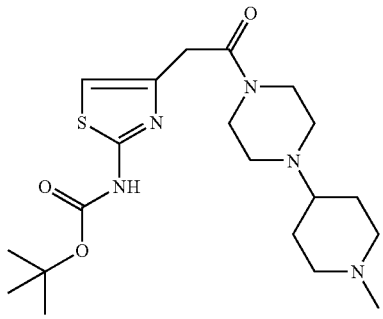

47.2 To a stirred suspension of 3.9 g (4-{2-[4-(1-methyl-piperidin-4-yl)-piperazin-1-yl]-2-oxo-ethyl}-thiazol-2-yl)-carbamic acid tert-butyl ester was added 40 ml of 33% HBr in acetic acid. The reaction mixture was stirred at r.t. for 4 h. The mixture was left overnight in the fridge. Then it was concentrated to leave an off-white solid which was suspended in 50 ml Et$_2$O, triturated and stirred at r.t. for 3 h. The product was collected by filtration, washed with Et$_2$O and dried to give 5.6 g 2-(2-amino-thiazol-4-yl)-1-[4-(1-methyl-piperidin-4-yl)-piperazin-1-yl]-ethanone trihydrobromide. Off-white solid. MS 324.4 ([M+H]$^+$)

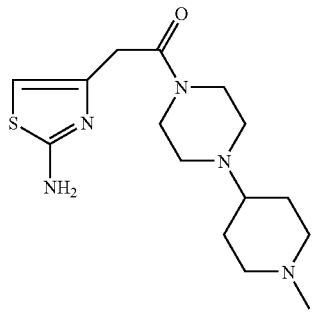

47.3 Using general procedure D, 2-(2-amino-thiazol-4-yl)-1-[4-(1-methyl-piperidin-4-yl)-piperazin-1-yl]-ethanone trihydrobromide was coupled with 5-bromothiophene-2-carboxylic acid to give 5-bromo-thiophene-2-carboxylic acid (4-{2-[4-(1-methyl-piperidin-4-yl)-piperazin-1-yl]-2-oxo-ethyl}-thiazol-2-yl)-amide. Yellow solid. MS 514.3 ([M+H]$^+$)

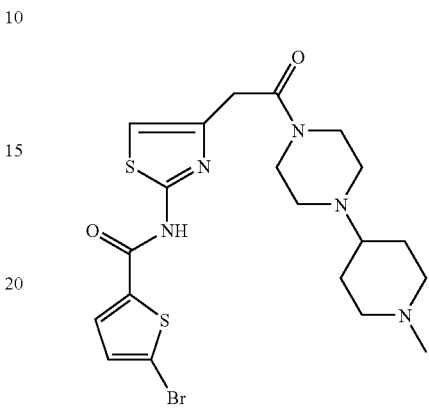

Example 48

In analogy to example 47.3, 2-(2-amino-thiazol-4-yl)-1-[4-(1-methyl-piperidin-4-yl)-piperazin-1-yl]-ethanone trihydrobromide (example 47.2) was coupled with 5-chlor-thiophene-2-carboxylic acid, using general method D, to give 5-chloro-thiophene-2-carboxylic acid (4-{2-[4-(1-methyl-piperidin-4-yl)-piperazin-1-yl]-2-oxo-ethyl}-thiazol-2-yl)-amide. Light orange solid. MS 468.5 ([M+H]$^+$)

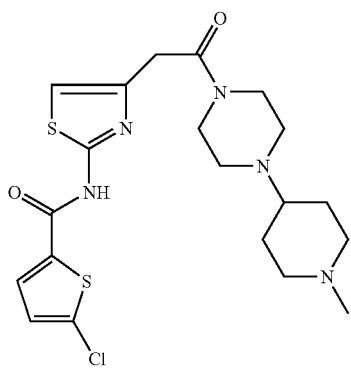

Example 49

In analogy to example 47.3, 2-(2-amino-thiazol-4-yl)-1-[4-(1-methyl-piperidin-4-yl)-piperazin-1-yl]-ethanone trihydrobromide (example 47.2) was coupled with 5-methylthiophene-2-carboxylic acid, using general method D, to give 5-methyl-thiophene-2-carboxylic acid (4-{2-[4-(1-methyl-piperidin-4-yl)-piperazin-1-yl]-2-oxo-ethyl}-thiazol-2-yl)-amide. Light yellow solid. MS 448.4 ([M+H]$^+$)

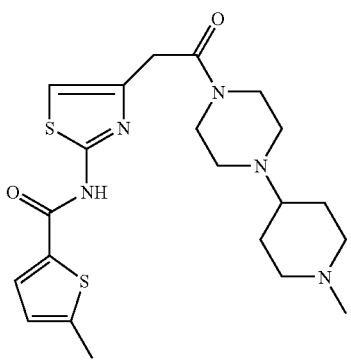

Example 50

In analogy to example 47.3, 2-(2-amino-thiazol-4-yl)-1-[4-(1-methyl-piperidin-4-yl)-piperazin-1-yl]-ethanone trihydrobromide (example 47.2) was coupled with 3-fluoro-4-methoxybenzoic acid, using general method D, to give 3-fluoro-4-methoxy-N-(4-{2-[4-(1-methyl-piperidin-4-yl)-piperazin-1-yl]-2-oxo-ethyl}-thiazol-2-yl)-benzamide. Off-white amorphous solid. MS 476.3 ([M+H]$^+$)

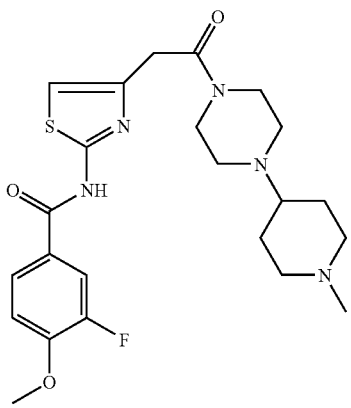

Example 51

51.1 Using general method A, 5-chlorothiophene-2-carboxylic acid and ethyl-2-amino-4-thiazole acetate were coupled to give {2-[(5-chloro-thiophene-2-carbonyl)-amino]-thiazol-4-yl}-acetic acid ethyl ester. Off-white solid. MS 331.3 ([M+H]$^+$)

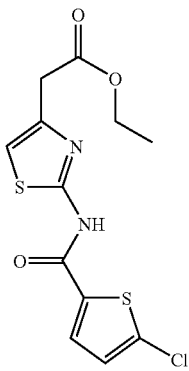

51.2 Using general method F, 5-chlorothiophene-2-carboxylic acid and ethyl-2-amino-4-thiazole acetate was reacted with 1-(4-amino-3-fluoro-phenyl)-1H-pyridin-2-one (CAS 536747-52-1, prepared according to C. F. Bigge et al., patent application WO 2003045912) to give 5-chloro-thiophene-2-carboxylic acid (4-{[2-fluoro-4-(2-oxo-2H-pyridin-1-yl)-phenylcarbamoyl]-methyl}-thiazol-2-yl)-amide. Light yellow solid. MS 489.3 ([M+H]$^+$)

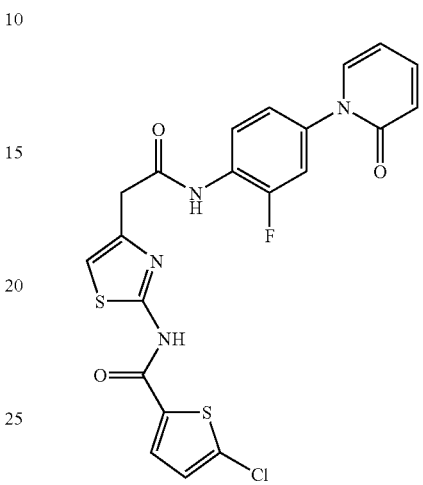

Example 52

In analogy to example 51.2, {2-[(5-chloro-thiophene-2-carbonyl)-amino]-thiazol-4-yl}-acetic acid ethyl ester (example 51.1) was reacted with 4-(4-amino-3-fluoro-phenyl)-morpholin-3-one (CAS 742073-22-9) to give {2-[(5-chloro-thiophene-2-carbonyl)-amino]-thiazol-4-yl}-acetic acid ethyl ester. Light yellow solid. MS 495.4 ([M+H]$^+$)

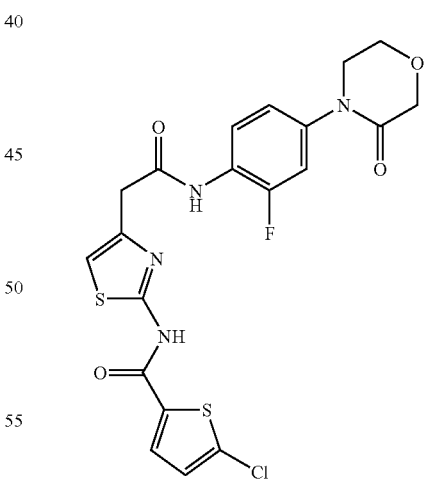

Example 53

53.1 Using general method E, {2-[(5-chloro-thiophene-2-carbonyl)-amino]-thiazol-4-yl}-acetic acid ethyl ester (example 51.1) was hydrolyzed to give {2-[(5-chloro-thiophene-2-carbonyl)-amino]-thiazol-4-yl}-acetic acid. Off-white solid. MS 301.0 ([M−H]$^−$)

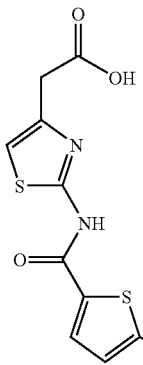

53.2 Using general method A, {2-[(5-chloro-thiophene-2-carbonyl)-amino]-thiazol-4-yl}-acetic acid was coupled with 1-methyl-4-(piperidin-4-yl)-piperazine to give 5-chloro-thiophene-2-carboxylic acid (4-{2-[4-(4-methyl-piperazin-1-yl)-piperidin-1-yl]-2-oxo-ethyl}-thiazol-2-yl)-amide. Light yellow amorphous solid. MS 468.4 ([M+H]$^+$)

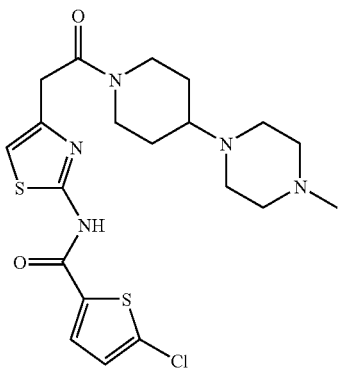

Example 54

54.1 Using general method A, with THF instead of DMF as solvent, [2-(4-chloro-benzoylamino)-thiazol-4-yl]-acetic acid ethyl ester (example 1.1) was coupled with tert-butyl-1-piperazine carboxylate to give 4-{2-[2-(4-chloro-benzoylamino)-thiazol-4-yl]-acetyl}-piperazine-1-carboxylic acid tert-butyl ester. White solid. MS 465.1 ([M+H]$^+$)

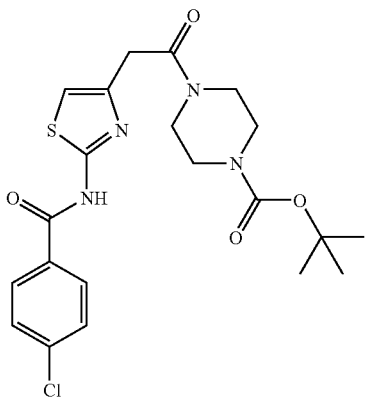

54.2 In analogy to example 33, 4-{2-[2-(4-chloro-benzoylamino)-thiazol-4-yl]-acetyl}-piperazine-1-carboxylic acid tert-butyl ester was deprotected to give 4-chloro-N-[4-(2-oxo-2-piperazin-1-yl-ethyl)-thiazol-2-yl]-benzamide. White solid. MS 365.1 ([M+H]$^+$)

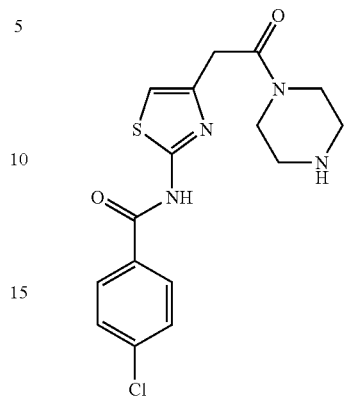

54.3 Using general procedure A, 4-chloro-N-[4-(2-oxo-2-piperazin-1-yl-ethyl)-thiazol-2-yl]-benzamide was coupled with (2-oxo-pyrrolidine-1-yl)-acetic acid (CAS 53934-76-2) to give 4-chloro-N-[4-(2-oxo-2-{4-[2-(2-oxo-pyrrolidin-1-yl)-acetyl]-piperazin-1-yl}-ethyl)-thiazol-2-yl]-benzamide. White solid. MS 490.4 ([M+H]$^+$)

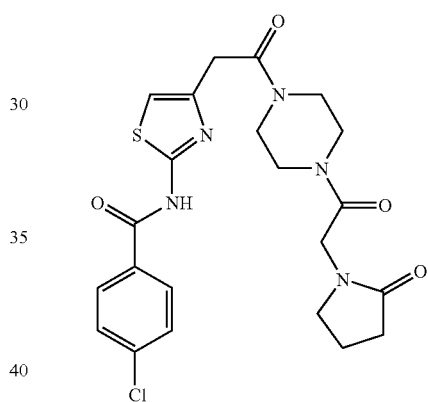

Example 55

55.1 Using general method A, with THF instead of DMF as solvent, 4-chloro-N-[4-(2-oxo-2-piperazin-1-yl-ethyl)-thiazol-2-yl]-benzamide (example 54.2) was coupled with bromoacetic acid to give N-(4-{2-[4-(2-bromo-acetyl)-piperazin-1-yl]-2-oxo-ethyl}-thiazol-2-yl)-4-chloro-benzamide. Amorphous white solid.

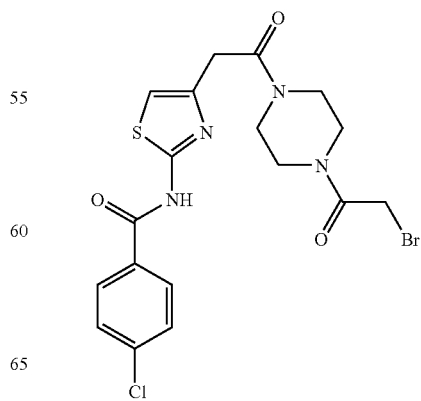

55.2 To a stirred mixture of 100 mg N-(4-{2-[4-(2-bromo-acetyl)-piperazin-1-yl]-2-oxo-ethyl}-thiazol-2-yl)-4-chloro-benzamide in 5 ml THF at r.t. were added 0.04 ml (aminomethyl)cyclohexane and 0.09 ml triethylamine. After 48 hrs stirring at r.t. under argon atmosphere, the reaction mixture was concentrated. The crude product was purified by chromatography on silica using a gradient from $CH_2Cl_2$ to $CH_2Cl_2$/MeOH 95:5 in 20 min to give 19 mg 4-chloro-N-[4-(2-{4-[2-(cyclohexylmethyl-amino)-acetyl]-piperazin-1-yl}-2-oxo-ethyl)-thiazol-2-yl]-benzamide. White solid. MS 518.5 ([M+H]$^+$)

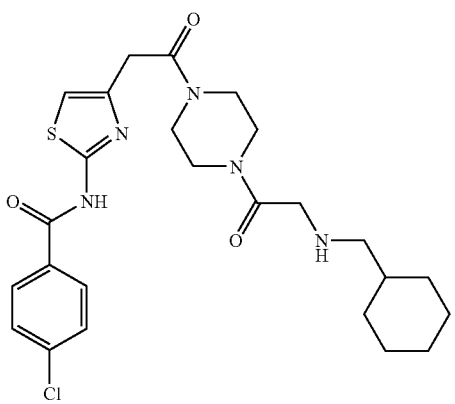

Example 56

In analogy to example 55.2, N-(4-{2-[4-(2-bromo-acetyl)-piperazin-1-yl]-2-oxo-ethyl}-thiazol-2-yl)-4-chloro-benzamide was reacted with pyrrolidine to give 4-chloro-N-(4-{2-oxo-2-[4-(2-pyrrolidin-1-yl-acetyl)-piperazin-1-yl]-ethyl}-thiazol-2-yl)-benzamide. Off-white amorphous solid. MS 476.0 ([M+H]$^+$)

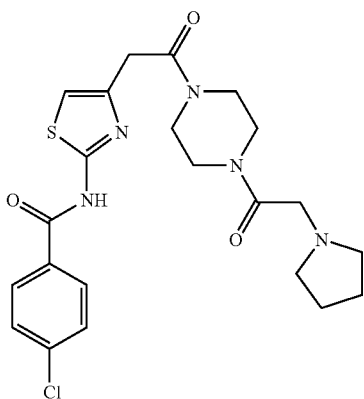

Example 57

57.1 To a stirred, cooled (0° C.) solution of the 1.6 g 3-aminopyrazole in DMF under an argon atmosphere was added potassium tert-butylate. After 30 min. stirring at 0° C., ethyl iodoacetate was added in one portion. After 2 h stirring at 0° C., the ice bath was removed and stirring at r.t. was continued for 22 h. The mixture was concentrated in order to remove as much DMF as possible. The residue was taken up in EtOAc and washed with $H_2O$. The aqueous phase was extracted with EtOAc. The combined organics were washed with $H_2O$ and brine, dried (MgSO$_4$), filtered and concentrated. The crude product was purified by chromatography on silica using a gradient from cyclohexane to EtOAc in 40 min to give 366 mg (3-amino-pyrazol-1-yl)-acetic acid ethyl ester as viscous yellow oil.

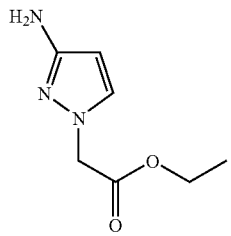

57.2 Using general method A, with THF instead of DMF as solvent, (3-amino-pyrazol-1-yl)-acetic acid ethyl ester was coupled with 5-chlorothiophene-2-carboxylic acid to give {3-[(5-chloro-thiophene-2-carbonyl)-amino]-pyrazol-1-yl}-acetic acid ethyl ester. Light yellow solid. MS 314.0 ([M+H]$^+$)

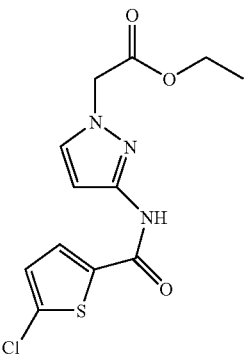

57.3 Using general method E, {3-[(5-chloro-thiophene-2-carbonyl)-amino]-pyrazol-1-yl}-acetic acid ethyl ester was hydrolyzed to give {3-[(5-chloro-thiophene-2-carbonyl)-amino]-pyrazol-1-yl}-acetic acid. Off-white powder. MS 284.0 ([M−H]$^-$)

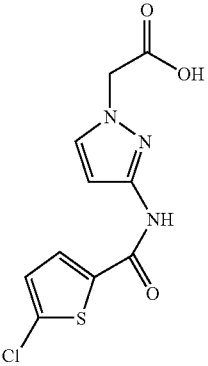

57.4 According to general method B, {3-[(5-chloro-thiophene-2-carbonyl)-amino]-pyrazol-1-yl}-acetic acid was reacted with 1-(4-amino-3-fluoro-phenyl)-1H-pyridin-2-one (CAS 536747-52-1, prepared according to C. F. Bigge et al., patent application WO 2003045912) to give 5-chloro-thiophene-2-carboxylic acid (1-{[2-fluoro-4-(2-oxo-2H-pyridin-1-yl)-phenylcarbamoyl]-methyl}-1H-pyrazol-3-yl)-amide. White solid. MS 472.4 ([M+H]$^+$)

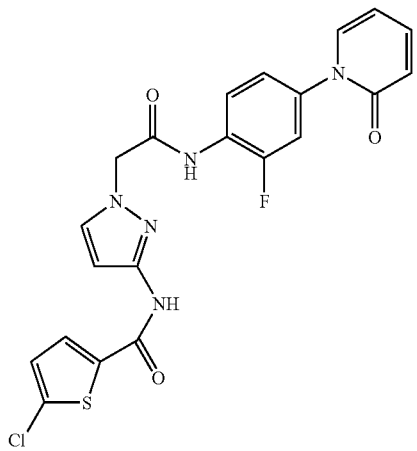

Example 58

Using general method A, using THF instead of DMF as solvent, {3-[(5-chloro-thiophene-2-carbonyl)-amino]-pyrazol-1-yl}-acetic acid (example 57.3) was reacted with 1-(N-methyl-4-piperidyl)-piperazine to give 5-chloro-thiophene-2-carboxylic acid (1-{2-[4-(1-methyl-piperidin-4-yl)-piperazin-1-yl]-2-oxo-ethyl}-1H-pyrazol-3-yl)-amide. Off-white solid. MS 451.3 ([M+H]$^+$)

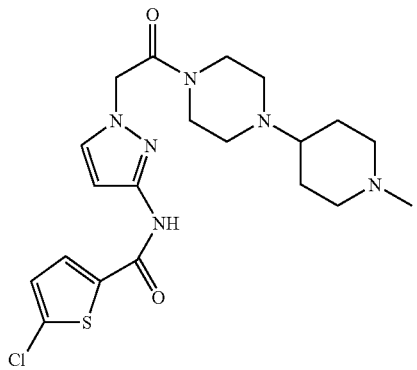

Example 59

59.1 Using general method A, with THF instead of DMF as solvent, (3-amino-pyrazol-1-yl)-acetic acid ethyl ester (example 57.1) was coupled with 4-chlorobenzoic acid to give [3-(4-chloro-benzoylamino)-pyrazol-1-yl]-acetic acid ethyl ester. Off-white solid. MS 308.3 ([M+H]$^+$)

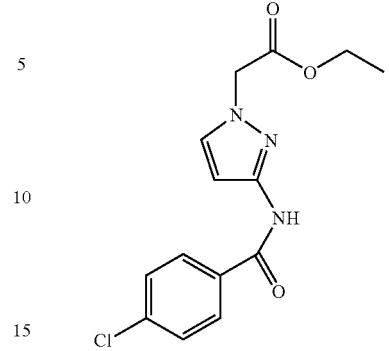

59.2 Using general method E, [3-(4-chloro-benzoylamino)-pyrazol-1-yl]-acetic acid ethyl ester was hydrolyzed to give [3-(4-chloro-benzoylamino)-pyrazol-1-yl]-acetic acid. White powder. MS 278.0 ([M−H]$^-$)

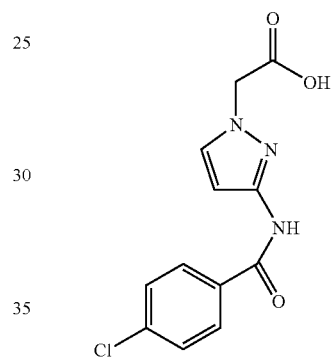

59.3 According to general method B, [3-(4-chloro-benzoylamino)-pyrazol-1-yl]-acetic acid was reacted with 1-(4-amino-3-fluoro-phenyl)-1H-pyridin-2-one (CAS 536747-52-1, prepared according to C. F. Bigge et al., patent application WO 2003045912) to give 4-chloro-N-(1-{[2-fluoro-4-(2-oxo-2H-pyridin-1-yl)-phenylcarbamoyl]-methyl}-1H-pyrazol-3-yl)-benzamide. White solid. MS 466.3 ([M+H]$^+$)

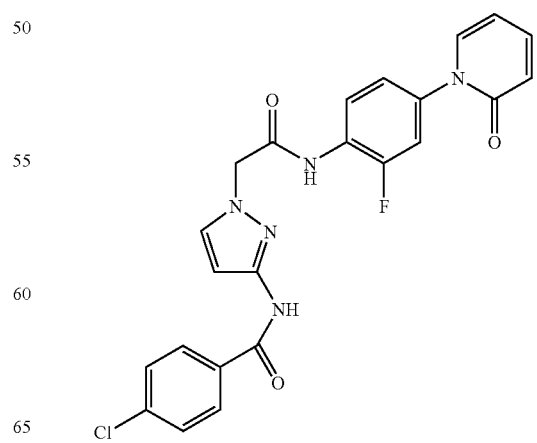

Example 60

Using general method A, using THF instead of DMF as solvent, [3-(4-chloro-benzoylamino)-pyrazol-1-yl]-acetic acid (example 59.2) was reacted with 1-(N-methyl-4-piperidyl)-piperazine to give 4-chloro-N-(1-{2-[4-(1-methyl-piperidin-4-yl)-piperazin-1-yl]-2-oxo-ethyl}-1H-pyrazol-3-yl)-benzamide. Off-white solid. MS 445.4 ([M+H]⁺)

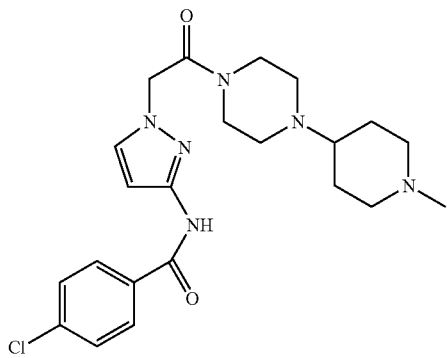

Example 61

61.1 To a stirred mixture of 2.8 g 3-amino-1,2,4-triazole in 50 ml DMF, 1.57 g NaH were slowly added at 0° C. under an argon atmosphere. After 1 hr stirring at 0° C., 3.31 ml ethyliodoacetate were added. The reaction mixture was stirred at r.t. over night. The mixture was diluted with water and extracted with EtOAc and CH$_2$Cl$_2$/MeOH 9:1. The organic phase was dried (MgSO4), filtered and concentrated. The crude product was purified by chromatography on silica, using a gradient from CH$_2$Cl$_2$ to CH$_2$Cl$_2$/MeOH 9:1 and then crystallization from cyclohexane/EtOAc to give 750 mg (3-amino-[1,2,4]triazol-1-yl)-acetic acid ethyl ester as a white solid.

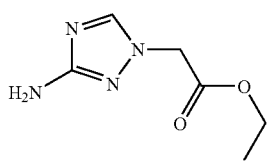

61.2 Using general method A, (3-amino-[1,2,4]triazol-1-yl)-acetic acid ethyl ester was coupled with 5-chlorothiophene-2-carboxylic acid to give {3-[(5-chloro-thiophene-2-carbonyl)-amino]-[1,2,4]triazol-1-yl}-acetic acid ethyl ester. Off-white solid. MS 315.1 ([M+H]⁺)

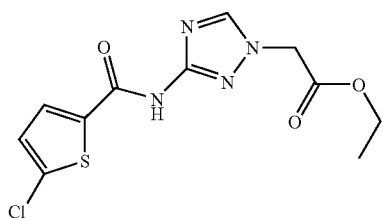

61.3 Using general method E, {3-[(5-chloro-thiophene-2-carbonyl)-amino]-[1,2,4]triazol-1-yl}-acetic acid ethyl ester was hydrolyzed to give {3-[(5-chloro-thiophene-2-carbonyl)-amino]-[1,2,4]triazol-1-yl}-acetic acid. Off-white powder. MS 285.0 ([M−H]⁻)

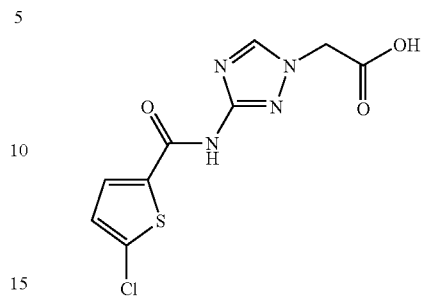

61.4 According to general method B, {3-[(5-chloro-thiophene-2-carbonyl)-amino]-[1,2,4]triazol-1-yl}-acetic acid was reacted with 1-(4-amino-3-fluoro-phenyl)-1H-pyridin-2-one (CAS 536747-52-1, prepared according to C. F. Bigge et al., patent application WO 2003045912) to give 5-chloro-thiophene-2-carboxylic acid (1-{[2-fluoro-4-(2-oxo-2H-pyridin-1-yl)-phenylcarbamoyl]-methyl}-1H-[1,2,4]triazol-3-yl)-amide. Off-white solid. MS 473.4 ([M+H]⁺)

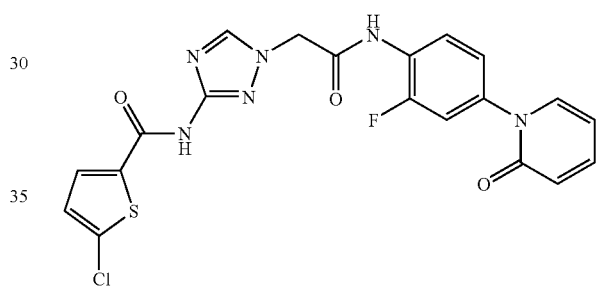

Example 62

Using general method A, using THF instead of DMF as solvent, {3-[(5-chloro-thiophene-2-carbonyl)-amino]-[1,2,4]triazol-1-yl}-acetic acid (example 61.3) was reacted with 1-(N-methyl-4-piperidyl)-piperazine to give 5-chloro-thiophene-2-carboxylic acid (1-{2-[4-(1-methyl-piperidin-4-yl)-piperazin-1-yl]-2-oxo-ethyl}-1H-[1,2,4]triazol-3-yl)-amide. Off-white solid. MS 452.3 ([M+H]⁺)

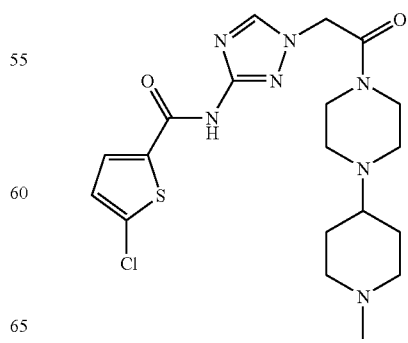

Example 63

63.1 A solution of 8.5 g 5-amino-1H-tetrazole, 8.8 ml methyl chloroacetate and 5.8 g potassium hydroxide in 100 ml methanol was heated to reflux under an argon atmosphere and stirred for 18 h. A white solid slowly precipitated. The suspension was cooled to r.t. The white solid was filtered off and washed with methanol. The filtrate was concentrated. The residue was suspended in 100 ml EtOH and heated to reflux. After 1 h stirring at reflux, the mixture was filtered while hot. The filtrate was concentrated. The residue was recrystallized in 100 ml EtOH to give 1.8 g of (5-amino-tetrazol-2-yl)-acetic acid methyl ester as colorless crystalline solid.

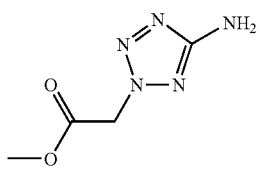

63.2 Using general method D, (5-amino-tetrazol-2-yl)-acetic acid methyl ester was coupled with 5-chlorothiophene-2-carboxylic acid to give {5-[(5-chloro-thiophene-2-carbonyl)-amino]-tetrazol-2-yl}-acetic acid methyl ester. White solid. MS 302.0 ([M+H]$^+$)

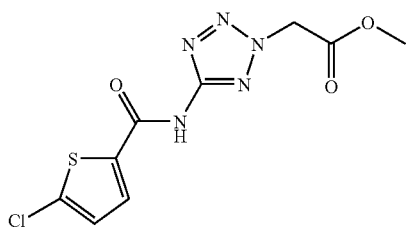

63.3 Using general method F, {5-[(5-chloro-thiophene-2-carbonyl)-amino]-tetrazol-2-yl}-acetic acid methyl ester was reacted with 1-(4-amino-3-fluoro-phenyl)-1H-pyridin-2-one (CAS 536747-52-1, prepared according to C. F. Bigge et al., patent application WO 2003045912) to give 5-chloro-thiophene-2-carboxylic acid (2-{[2-fluoro-4-(2-oxo-2H-pyridin-1-yl)-phenylcarbamoyl]-methyl}-2H-tetrazol-5-yl)-amide. Off-white solid. MS 474.3 ([M+H]$^+$)

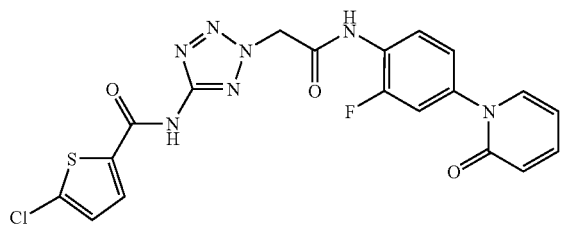

Example 64

64.1 A solution of 1-(4-amino-3-fluoro-phenyl)-1H-pyridin-2-one (CAS 536747-52-1, prepared according to C. F. Bigge et al., patent application WO 2003045912) in 150 ml THF was treated with 5.8 ml triethylamine and 3.2 ml bromoacetyl bromide. The reaction mixture was stirred overnight at r.t., then again treated with 2.1 ml bromoacetyl bromide. After stirring overnight at r.t., the solid was filtered off and washed with THF. Then it was dissolved 11 EtOAc and washed 2× with 100 ml H$_2$O. The organic layer was dried over MgSO$_4$, filtered and concentrated to give 3.0 g 2-bromo-[2-fluoro-4-(2-oxo-pyridin-1-yl)-phenyl]-acetamide as off-white solid. MS 325.1 ([M+H]$^+$)

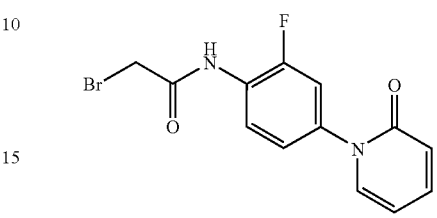

64.2 A suspension of 34 mg sodium hydride in 2 ml DMF was cooled to 0° C. and treated portionwise with 100 mg of 2-hydroxy-3-nitropyridine. The reaction mixture was stirred for 30 min, then treated at 0° C. with 0.244 mg 2-bromo-[2-fluoro-4-(2-oxo-pyridin-1-yl)-phenyl]-acetamide. The reaction mixture was stirred over night at r.t., then diluted with EtOAc and washed with water. The organic layer was dried (MgSO$_4$), filtered and concentrated. The crude product was purified by chromatography (silica gel, gradient CH$_2$Cl$_2$->CH$_2$Cl$_2$/MeOH 95:5) to give 61 mg [2-fluoro-4-(2-oxo-pyridin-1-yl)-phenyl]-2-(3-nitro-2-oxo-pyridin-1-yl)-acetamide as a light yellow solid. MS 385.1 ([M+H]$^+$)

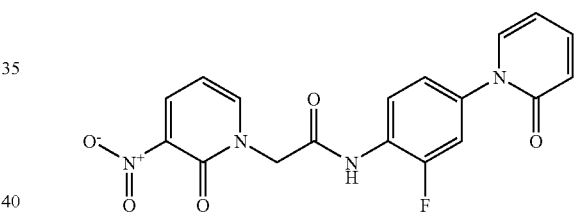

64.3 A suspension of 60 mg [2-fluoro-4-(2-oxo-pyridin-1-yl)-phenyl]-2-(3-nitro-2-oxo-pyridin-1-yl)-acetamide in 1 ml acetic acid was treated portionwise with 82 mg activated zinc powder. The reaction mixture was stirred for 3 hrs at r.t. The solid was filtered off and washed carefully with EtOH. The filtrate was concentrated. The crude product was purified by chromatography (silica, gradient CH$_2$Cl$_2$->CH$_2$Cl$_2$/MeOH 95:5) to give 39 mg 2-(3-amino-2-oxo-pyridin-1-yl)-[2-fluoro-4-(2-oxo-pyridin-1-yl)-phenyl]-acetamide as off-white solid. MS 355.0 ([M+H]$^+$)

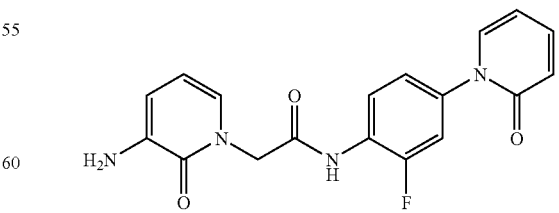

64.4 Using general method A, 2-(3-amino-2-oxo-pyridin-1-yl)-[2-fluoro-4-(2-oxo-pyridin-1-yl)-phenyl]-acetamide was reacted with 5-chloro-thiophene-2-carboxylic acid to give 5-chloro-thiophene-2-carboxylic acid (1-{[2-fluoro-4-

(2-oxo-pyridin-1-yl)-phenyl-carbamoyl]-methyl}-2-oxo-1,2-dihydro-pyridin-3-yl)-amide. Off-white solid. MS 499.3 ([M+H]⁺)

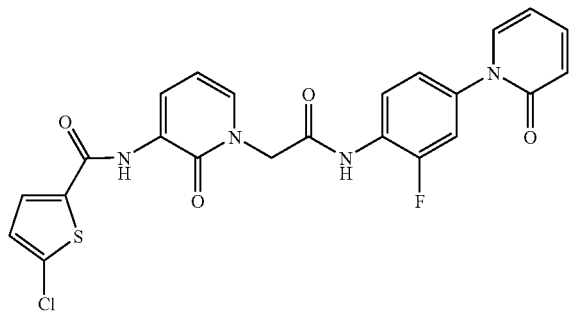

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxyde (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water.

The granulate is mixed with magnesiumstearate and the flavouring additives and filled into sachets.

Example F

Factor Xa activity was measured spectrophotometrically in microtiter plates in a final volume of 150 μl using the following conditions: Inhibition of human factor Xa (Enzyme Research Laboratories) was tested at an enzyme concentration of 3 nM using the chromogenic substrate S-2222 (Chromogenix AB, Mölndal, Sweden) at 200 nM. The reaction kinetics of the enzyme and the substrate were linear with both time and the enzyme concentration. The inhibitors were dissolved in DMSO and tested at various concentrations up to 100 μM. The inhibitors were diluted using HNPT buffer consisting of HEPES 100 mM, NaCl 140 mM, PEG 6000 0.1% and Tween 80 0.02%, pH 7.8. The cleavage of S-2222 by human factor Xa was followed at 405 nm for 5 minutes at room temperature.

The velocity of the reaction was determined by the autoreader from the slope of the linear regression fit to 7 time points (1 minute). The initial velocity for each inhibitor concentration was determined by the slope of at least 4 time points in the linear phase by a linear regression fit (mOD/min$^2$). Apparent dissociation constants $K_i$ were calculated according to Cheng and Prusoff [Cheng, Y. C.; Prusoff, W. H. Relationship between the inhibition constant ($K_i$) and the concentration of the inhibitor that causes 50 percent inhibition ($IC_{50}$) of an enzyme reaction. Biochem. Pharmacol. 1973, 22, 3099-3108.] based on the $IC_{50}$ and the respective $K_m$, determined previously ($K_i=IC_{50}/(I+S/K_m)$). The $K_m$ for the substrate used was determined under the conditions of the test with at least 5 substrate concentrations ranging from 0.5 to 15 times $K_m$. [Lottenberg R, Hall J A, Blinder M, Binder E P, Jackson C M., The action of thrombin on peptide p-nitroanilide substrates. Substrate selectivity and examination of hydrolysis under different reaction conditions. Biochim Biophys Acta. 1983 Feb. 15; 742(3):539-57]. According to Eadie [Eadie G. S. The inhibition of cholinesterase by physostigmine and prostigmine. J. Biol. Chem. 1942, 146, 85-93.], the $K_m$ for S-2222 amounted to 613 μM.

| Example | Ki [μM] factor Xa |
|---------|-------------------|
| Ex. 37.5 | 0.062 |
| Ex. 47.3 | 0.026 |
| Ex. 61.4 | 0.006 |

The invention claimed is:
1. A compound of formula (I):

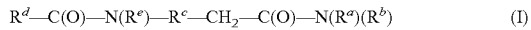

$$R^d—C(O)—N(R^e)—R^c—CH_2—C(O)—N(R^a)(R^b) \quad (I)$$

or a pharmaceutically acceptable salt thereof; wherein:
$R^a$ and $R^b$, together with the nitrogen atom to which they are attached, form piperazinyl-A-$R^{b3}$, wherein said piperazinyl is optionally substituted by halogen or $C_{1-6}$ alkyl; wherein:
A is a bond or —$CH_2$—$C(O)$—; and
$R^{b3}$ is selected from the group consisting of: (1) amino, optionally mono- or di-substituted by a substituent independently selected from the group consisting of $C_{1-6}$ alkyl, $C_{2-6}$ alkenyl and $C_{2-6}$ alkynyl, (2) aryl, (3) heteroaryl, (4) $C_{3-7}$ cycloalkyl and (5) heterocyclyl; wherein one or two carbon atoms of said aryl, heteroaryl, $C_{3-7}$ cycloalkyl or heterocyclyl is optionally replaced with a carbonyl group, and wherein said aryl, heteroaryl, $C_{3-7}$ cycloalkyl or heterocyclyl is optionally substituted by one or more substituents independently selected from the group consisting of:
$C_{1-6}$ alkyl, $C_{2-6}$ alkenyl, $C_{2-6}$ alkynyl, $C_{1-6}$ alkoxy, halogen, cyano, nitro, amino, mono- or di-$C_{1-6}$ alkyl substituted amino, hydroxy, hydroxy $C_{1-6}$ alkyl, aminocarbonyl, mono- or di-$C_{1-6}$ alkyl substituted aminocarbonyl, halo $C_{1-6}$ alkyl, $C_{1-6}$ alkylsulfonyl, $C_{1-6}$ alkylsulfinyl, $C_{1-6}$ alkylthio, amino $C_{1-6}$ alkyl, mono- or di-$C_{1-6}$ alkyl substituted amino $C_{1-6}$ alkyl, aminosulfonyl, and mono- or di-$C_{1-6}$ alkyl substituted amino sulfonyl;
$R^c$ is thiazole optionally substituted by one or more substituents independently selected from the group consisting of halogen and $C_{1-6}$ alkyl; and one or two carbon atoms of said thiazole is optionally replaced with a carbonyl group;
$R^d$ is heteroaryl or heterocyclyl; wherein said heteroaryl or heterocyclyl is optionally substituted by one or more substituents independently selected from the group consisting of halogen, $C_{1-6}$ alkyl and $C_{1-6}$ alkoxy;
$R^e$ is hydrogen or $C_{1-6}$ alkyl; and
$R^f$ is hydrogen or $C_{1-6}$ alkyl.

2. A compound according to claim 1, wherein said piperazinyl of piperazinyl-A-$R^{b3}$ is bound to -A-$R^{b3}$ at the 4-position.

3. A compound according to claim 1, wherein $R^{b3}$ is a heterocyclyl optionally substituted by one or more substituents independently selected from the group consisting of $C_{1-6}$ alkyl, $C_{1-6}$ alkoxy, amino, mono- or di-$C_{1-6}$ alkyl substituted amino, hydroxy, hydroxy $C_{1-6}$ alkyl, aminocarbonyl, mono- or di-$C_{1-6}$ alkyl substituted aminocarbonyl, halo $C_{1-6}$ alkyl, $C_{1-6}$ alkylsulfonyl, $C_{1-6}$ alkylsulfinyl, and $C_{1-6}$ alkylthio; wherein one or two carbon atoms of said heterocyclyl is optionally replaced with a carbonyl group.

4. A compound according to claim 1, wherein $R^{b3}$ is a heterocyclyl selected from the group consisting of piperidinyl, pyrrolidinyl, morpholinyl, piperazinyl and thiazolidinyl, wherein said heterocyclyl is optionally substituted by one or more substituents independently selected from the group consisting of $C_{1-6}$ alkyl, $C_{1-6}$ alkoxy, amino, mono- or di-$C_{1-6}$ alkyl substituted amino, hydroxy, hydroxy $C_{1-6}$ alkyl, aminocarbonyl, mono- or di-$C_{1-6}$ alkyl substituted aminocarbonyl, halo $C_{1-6}$ alkyl, $C_{1-6}$ alkylsulfonyl, $C_{1-6}$ alkylsulfinyl, and $C_{1-6}$ alkylthio; wherein one or two carbon atoms of said heterocyclyl is optionally replaced with a carbonyl group.

5. A compound according to claim 1 wherein $R^e$ is hydrogen.

6. A compound according to claim 1, wherein $R^C$ is unsubstituted thiazole.

7. A compound according to claim 1, wherein $R^d$ is thienyl optionally substituted by one or more substituents independently selected from the group consisting of halogen, $C_{1-6}$ alkyl and $C_{1-6}$ alkoxy.

8. A compound according to claim 1, wherein $R^d$ is chlorothienyl.

9. A compound according to claim 1 which is 5-chlorothiophene-2-carboxylic acid (4-{2-[4-(1-methyl-piperidin-4-yl)-piperazin-1-yl]-2-oxo-ethyl}-thiazol-2-yl)-amide.

10. A pharmaceutical composition comprising a compound according to claim 1 and a pharmaceutically acceptable excipient.

11. A compound according to claim 1, selected from the group consisting of:

5-chloro-thiophene-2-carboxylic acid (4-{2-oxo-2-[4-(2-oxo-2-pyrrolidin-1-yl-ethyl)-piperazin-1-yl]-ethyl}-thiazol-2-yl)-amide;

5-bromo-thiophene-2-carboxylic acid (4-{2-oxo-2-[4-(2-oxo-2-pyrrolidin-1-yl-ethyl)-piperazin-1-yl]-ethyl}-thiazol-2-yl)-amide;

5-methyl-thiophene-2-carboxylic acid (4-{2-oxo-2-[4-(2-oxo-2-pyrrolidin-1-yl-ethyl)-piperazin-1-yl]-ethyl}-thiazol-2-yl)-amide;

benzo[1,3]dioxole-5-carboxylic acid (4-{2-oxo-2-[4-(2-oxo-2-pyrrolidin-1-yl-ethyl)-piperazin-1-yl]-ethyl}-thiazol-2-yl)-amide;

1H-indole-6-carboxylic acid (4-{2-oxo-2-[4-(2-oxo-2-pyrrolidin-1-yl-ethyl)-piperazin-1-yl]-ethyl}-thiazol-2-yl)-amide;

5-chloro-pyridine-2-carboxylic acid (4-{2-oxo-2-[4-(2-oxo-2-pyrrolidin-1-yl-ethyl)-piperazin-1-yl]-ethyl}-thiazol-2-yl)-amide;

2,3-dihydro-benzofuran-5-carboxylic acid (4-{2-oxo-2-[4-(2-oxo-2-pyrrolidin-1-yl-ethyl)-piperazin-1-yl]-ethyl}-thiazol-2-yl)-amide;

5-bromo-thiophene-2-carboxylic acid (4-{2-[4-(1-methyl-piperidin-4-yl)-piperazin-1-yl]-2-oxo-ethyl}-thiazol-2-yl)-amide;

5-methyl-thiophene-2-carboxylic acid (4-{2-[4-(1-methyl-piperidin-4-yl)-piperazin-1-yl]-2-oxo-ethyl}-thiazol-2-yl)-amide; and a pharmaceutically acceptable salt thereof.

12. A compound according to claim 1 which is 5-chloro-thiophene-2-carboxylic acid (4-{2-oxo-2-[4-(2-oxo-2-pyrrolidin-1-yl-ethyl)-piperazin-1-yl]-ethyl}-thiazol-2-yl)-amide.

13. A compound according to claim 1 which is 5-bromo-thiophene-2-carboxylic acid (4-{2-oxo-2-[4-(2-oxo-2-pyrrolidin-1-yl-ethyl)-piperazin-1-yl]-ethyl}-thiazol-2-yl)-amide.

14. A compound according to claim 1 which is 5-methyl-thiophene-2-carboxylic acid (4-{2-oxo-2-[4-(2-oxo-2-pyrrolidin-1-yl-ethyl)-piperazin-1-yl]-ethyl}-thiazol-2-yl)-amide.

15. A compound according to claim 1 which is benzo[1,3]dioxole-5-carboxylic acid (4-{2-oxo-2-[4-(2-oxo-2-pyrrolidin-1-yl-ethyl)-piperazin-1-yl]-ethyl}-thiazol-2-yl)-amide.

16. A compound according to claim 1 which is 1H-indole-6-carboxylic acid (4-{2-oxo-2-[4-(2-oxo-2-pyrrolidin-1-yl-ethyl)-piperazin-1-yl]-ethyl}-thiazol-2-yl)-amide.

17. A compound according to claim 1 which is 5-chloro-pyridine-2-carboxylic acid (4-{2-oxo-2-[4-(2-oxo-2-pyrrolidin-1-yl-ethyl)-piperazin-1-yl]-ethyl}-thiazol-2-yl)-amide.

18. A compound according to claim 1 which is 2,3-dihydro-benzofuran-5-carboxylic acid (4-{2-oxo-2-[4-(2-oxo-2-pyrrolidin-1-yl-ethyl)-piperazin-1-yl]-ethyl}-thiazol-2-yl)-amide.

19. A compound according to claim 1 which is 5-bromo-thiophene-2-carboxylic acid (4-{2-[4-(1-methyl-piperidin-4-yl)-piperazin-1-yl]-2-oxo-ethyl}-thiazol-2-yl)-amide.

20. A compound according to claim 1 which is 5-methyl-thiophene-2-carboxylic acid (4-{2-[4-(1-methyl-piperidin-4-yl)-piperazin-1-yl]-2-oxo-ethyl}-thiazol-2-yl)-amide.

* * * * *